(12) United States Patent
Mahoney et al.

(10) Patent No.: US 10,828,527 B2
(45) Date of Patent: Nov. 10, 2020

(54) EXOSUIT SYSTEM SYSTEMS AND METHODS FOR ASSISTING, RESISTING AND ALIGNING CORE BIOMECHANICAL FUNCTIONS

(71) Applicant: SEISMIC HOLDINGS, INC., Menlo Park, CA (US)

(72) Inventors: Richard Mahoney, Los Altos, CA (US); Melinda Cromie Lear, Menlo Park, CA (US)

(73) Assignee: SEISMIC HOLDINGS, INC., Menlo Park, CA (US)

( * ) Notice: Subject to any disclaimer, the term of this patent is extended or adjusted under 35 U.S.C. 154(b) by 0 days.

(21) Appl. No.: 16/182,102

(22) Filed: Nov. 6, 2018

(65) Prior Publication Data
US 2019/0134454 A1    May 9, 2019

Related U.S. Application Data

(60) Provisional application No. 62/582,750, filed on Nov. 7, 2017.

(51) Int. Cl.
| | |
|---|---|
| A63B 21/00 | (2006.01) |
| A63B 24/00 | (2006.01) |
| A63B 71/06 | (2006.01) |
| A63F 13/211 | (2014.01) |
| A63F 13/212 | (2014.01) |
| A63F 13/24 | (2014.01) |
| A63F 13/285 | (2014.01) |

(Continued)

(52) U.S. Cl.
CPC ........ A63B 21/4025 (2015.10); A61B 5/0024 (2013.01); A61B 5/1114 (2013.01);
(Continued)

(58) Field of Classification Search
CPC ... A61B 5/1114; A61B 5/0024; A61B 5/6804; A61B 5/0022; A61B 5/7405; A61B 5/0476; A61B 5/0488; A61B 5/112; A61B 5/7435; A61B 5/7455; A61B 2562/0219; A61B 5/744; A61B 2505/09; A61B 5/1123; A63F 13/211; A63F 13/212; A63F 13/24;
(Continued)

(56) References Cited

U.S. PATENT DOCUMENTS

| | | | | |
|---|---|---|---|---|
| 4,724,827 A | * | 2/1988 | Schenck | A61H 1/0288 601/40 |
| 5,667,461 A | * | 9/1997 | Hall | A61H 1/0229 472/15 |

(Continued)

FOREIGN PATENT DOCUMENTS

| | | | |
|---|---|---|---|
| WO | 2016/138264 A1 | 9/2016 | |
| WO | WO-2016138264 A1 * | 9/2016 | A61H 1/02 |

*Primary Examiner* — Garrett K Atkinson
(74) *Attorney, Agent, or Firm* — Van Court & Aldridge LLP

(57) ABSTRACT

Exosuit systems and methods according to various embodiments are described herein. The exosuit system can be a suit that is worn by a wearer on the outside of his or her body. It may be worn under the wearer's normal clothing, over their clothing, between layers of clothing, or may be the wearer's primary clothing itself. The exosuit may be assistive, as it physically assists the wearer in performing particular activities, or can provide other functionality such as communication to the wearer through physical expressions to the body, engagement of the environment, or capturing of information from the wearer.

15 Claims, 27 Drawing Sheets

(51) Int. Cl.
*A63B 21/005* (2006.01)
*A61B 5/00* (2006.01)
*A61B 5/11* (2006.01)
*A61B 5/0476* (2006.01)
*A61B 5/0488* (2006.01)

(52) U.S. Cl.
CPC ........ *A61B 5/6804* (2013.01); *A63B 21/0058* (2013.01); *A63B 21/00178* (2013.01); *A63B 21/4027* (2015.10); *A63B 24/0006* (2013.01); *A63B 24/0062* (2013.01); *A63B 24/0087* (2013.01); *A63B 71/0622* (2013.01); *A63F 13/211* (2014.09); *A63F 13/212* (2014.09); *A63F 13/24* (2014.09); *A63F 13/285* (2014.09); *A61B 5/0022* (2013.01); *A61B 5/0476* (2013.01); *A61B 5/0488* (2013.01); *A61B 5/112* (2013.01); *A61B 5/1123* (2013.01); *A61B 5/744* (2013.01); *A61B 5/7405* (2013.01); *A61B 5/7435* (2013.01); *A61B 5/7455* (2013.01); *A61B 2505/09* (2013.01); *A61B 2562/0219* (2013.01); *A63B 2024/0015* (2013.01); *A63B 2071/0655* (2013.01); *A63B 2220/50* (2013.01); *A63B 2220/803* (2013.01); *A63B 2220/836* (2013.01); *A63B 2225/09* (2013.01); *A63B 2225/50* (2013.01); *A63B 2225/74* (2020.08)

(58) Field of Classification Search
CPC ............... A63F 13/285; A63B 21/4025; A63B 24/0062; A63B 24/0006; A63B 71/0622; A63B 21/00178; A63B 21/4027; A63B 21/0058; A63B 24/0087; A63B 2225/09; A63B 2071/0655; A63B 2220/50; A63B 2220/803; A63B 2220/836; A63B 2225/50; A63B 2024/0015; A63B 2207/02

See application file for complete search history.

(56) References Cited

U.S. PATENT DOCUMENTS

| | | | |
|---|---|---|---|
| 6,123,649 A * | 9/2000 | Lee | A63B 21/153 482/51 |
| 6,666,831 B1 * | 12/2003 | Edgerton | A61H 1/0237 600/587 |
| 6,796,926 B2 * | 9/2004 | Reinkensmeyer | A61B 5/1038 482/51 |
| 7,331,906 B2 * | 2/2008 | He | A61H 1/0237 482/69 |
| 7,494,450 B2 * | 2/2009 | Solomon | A61H 1/0229 482/51 |
| 7,887,471 B2 * | 2/2011 | McSorley | A63B 21/0552 482/136 |
| 7,935,036 B2 * | 5/2011 | Haynes | A63B 21/4025 482/121 |
| 7,998,040 B2 * | 8/2011 | Kram | A63B 21/4015 482/124 |
| 8,057,410 B2 * | 11/2011 | Angold | A61H 3/00 601/35 |
| 8,608,479 B2 * | 12/2013 | Liu | A61H 1/024 434/255 |
| 9,266,233 B2 * | 2/2016 | Kornbluh | B25J 9/104 |
| 2003/0064869 A1 * | 4/2003 | Reinkensmeyer | A61B 5/1038 482/100 |
| 2004/0087418 A1 * | 5/2004 | Eldridge | A63B 21/157 482/54 |
| 2004/0204294 A2 * | 10/2004 | Wilkinson | A63B 21/015 482/54 |
| 2005/0101448 A1 * | 5/2005 | He | A61H 1/0237 482/54 |
| 2008/0300118 A1 * | 12/2008 | Wehrell | A63B 21/04 482/129 |
| 2010/0204804 A1 * | 8/2010 | Garrec | A61H 1/0277 623/24 |
| 2011/0313331 A1 * | 12/2011 | Dehez | A61H 1/0277 601/33 |
| 2012/0041513 A1 * | 2/2012 | Tucker | A61N 1/36003 607/48 |
| 2012/0058861 A1 * | 3/2012 | Satut | A63B 23/0244 482/8 |
| 2013/0130866 A1 * | 5/2013 | Wehrell | A61H 1/0229 482/5 |
| 2013/0225371 A1 * | 8/2013 | Harrer | A63B 21/0552 482/8 |
| 2014/0277739 A1 * | 9/2014 | Kornbluh | B25J 9/1615 700/260 |
| 2015/0173993 A1 * | 6/2015 | Walsh | B25J 9/0006 414/4 |
| 2015/0297934 A1 * | 10/2015 | Agrawal | A61H 1/0266 482/4 |

* cited by examiner

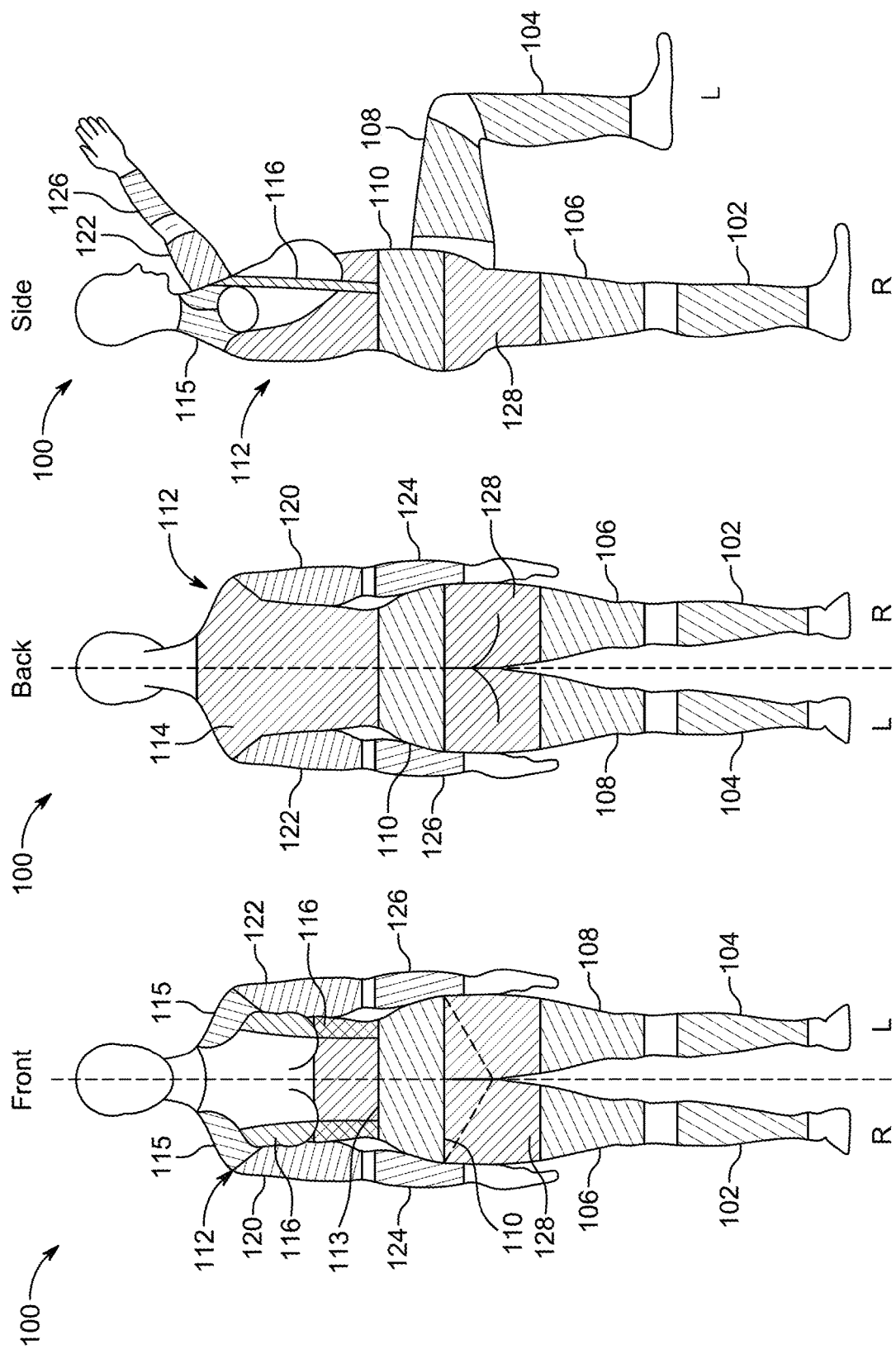

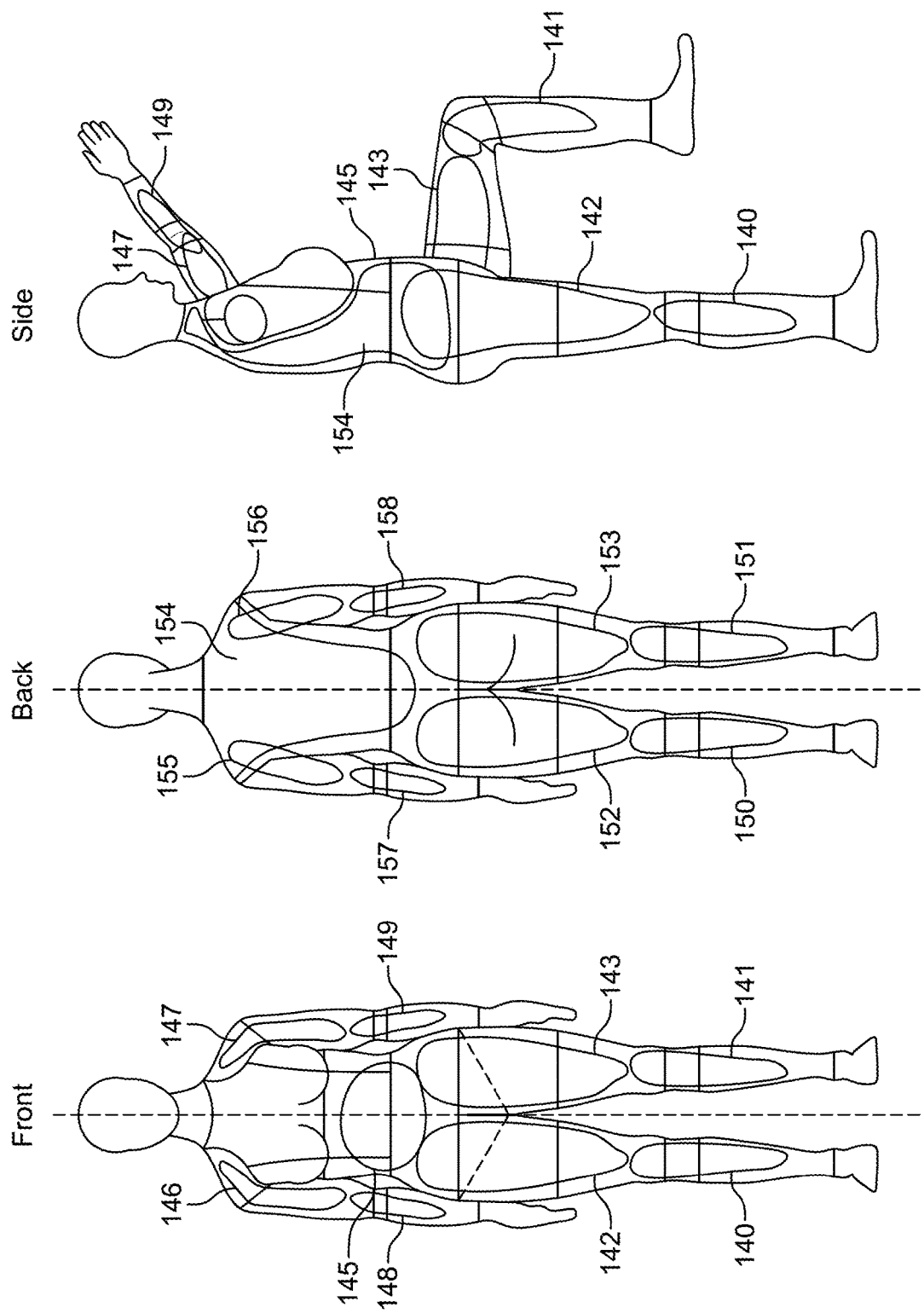

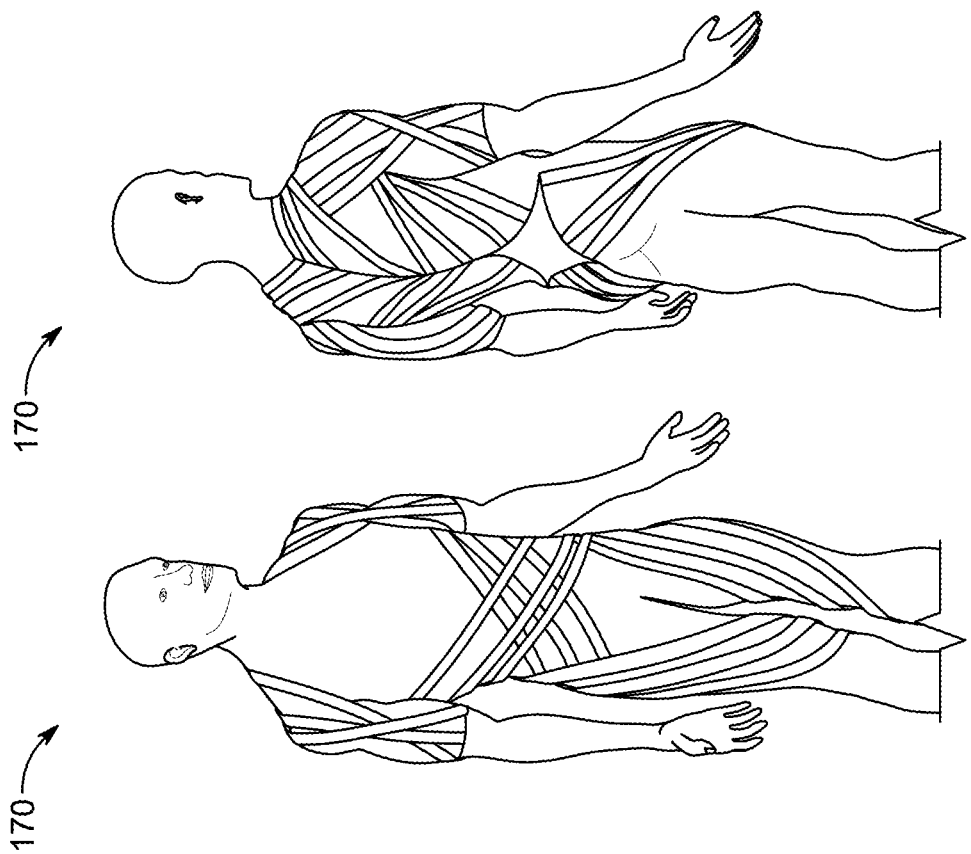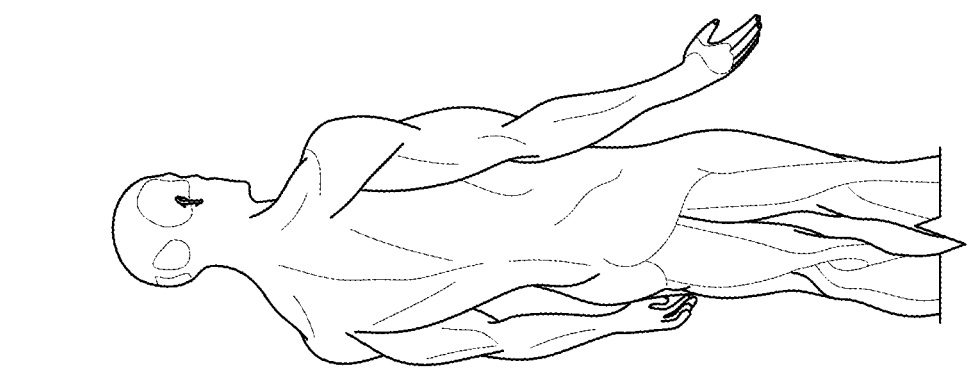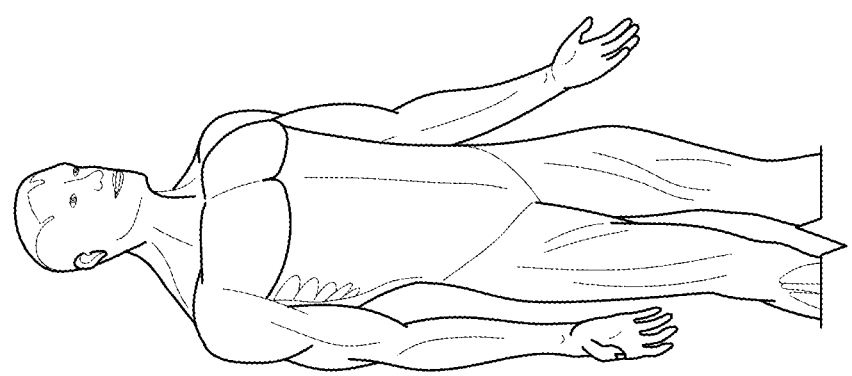

EXOSUIT SYSTEM SYSTEMS AND METHODS FOR ASSISTING, RESISTING AND ALIGNING CORE BIOMECHANICAL FUNCTIONS

CROSS-REFERENCE TO RELATED APPLICATION

This disclosure claims the benefit of U.S. Provisional Application No. 62/582,750, filed Nov. 7, 2017, the disclosure of which is incorporated herein in its entirety.

BACKGROUND

Humans exercise to stay in shape, develop muscle tone, and to increase or maintain overall wellness. Individuals may exercise in a gym, outdoors, or at home. The individual may perform an exercise routine that includes one or more specific exercise moves. Some of these moves may require the individual to maintain proper form to maximize effectiveness of the movement and to prevent injury.

SUMMARY

Exosuit systems and methods according to various embodiments are described herein. The exosuit system can be a suit that is worn by a wearer on the outside of his or her body. It may be worn under the wearer's normal clothing, over their clothing, between layers of clothing, or may be the wearer's primary clothing itself. The exosuit may be assistive, as it physically assists the wearer in performing particular activities, or can provide other functionality such as communication to the wearer through physical expressions to the body, engagement of the environment, or capturing of information from the wearer. The exosuit may also resist the wearer's motions as an exercise.

An exercise assistance system for use on a human body is provided in an embodiment. The system includes an exosuit configured to be worn on the human body as a garment, the exosuit including a plurality of sensors, a plurality of power layer segments that mimic musculature anatomy and movements of the human body, communications circuitry, and control circuitry coupled to the communications circuitry, the plurality of sensors, and the power layer segments. The control circuitry is operative to receive, via the communications circuitry, a user designated exercise program including at least one exercise movement, and selectively activate and deactivate at least one of the plurality of power layer segments to apply exosuit enabled resistance to a user of the exosuit when the user performs the at least one exercise movement.

According to an embodiment, the plurality of power layer segments are operative to apply varying levels of resistance to the user.

According to an embodiment, the at least one exercise movement requires activation of protagonist muscles, and wherein a subset of the power layer segments emulate activation of antagonist muscles associated with the at least one exercise movement to provide the resistance.

According to an embodiment, each of the plurality of power layer segments includes an array of flexible linear actuators that are secured to load distribution members.

According to an embodiment, each of the plurality of power layer segments includes a flexible linear actuator that is secured to load distribution members.

According to an embodiment, each of the plurality of power layer segments includes a flexdrive subsystem that is secured to a first load distribution member, a twisted string coupled to the flexdrive subsystem and secured to a second load distribution member, and power/communication lines coupled to the flexdrive subsystem.

According to an embodiment, the twisted string is aligned in conjunction with a muscle of the user.

An exercise assistance system for use on a human body is provided in another embodiment. The system can include an exosuit configured to be worn on the human body as a next-to-skin garment, the exosuit including a plurality of sensors, a plurality of power layer segments that mimic musculature anatomy and movements of the human body, communications circuitry, and control circuitry coupled to the communications circuitry, the plurality of sensors, and the power layer segments. The control circuitry is operative to monitor the plurality of sensors while a user of the exosuit is performing an exercise movement to obtain exercise factors, analyze the exercise factors to determine whether the user is performing the exercise movement within parameters associated with the exercise movement, and communicate feedback that indicates whether the user is performing the exercise movement factors within the parameters.

According to an embodiment, the communicated feedback comprises audio feedback, visual feedback, or haptic feedback.

According to an embodiment, the control circuitry is operative to selectively activate a subset of the plurality of power layer segment to reposition the user to a correct alignment in response to a determination that the exercise factors are not within the parameters.

According to an embodiment, the exercise factors comprise movement factors and form factors.

According to an embodiment, the exercise factors are adjusted to compensate for dimensions of the user of the exosuit.

According to an embodiment, each of the plurality of power layer segments includes a flexdrive subsystem that is secured to a first load distribution member, a twisted string coupled to the flexdrive subsystem and secured to a second load distribution member, and power/communication lines coupled to the flexdrive subsystem.

An exercise assistance system for use on a human body is provided. The system can include an exosuit configured to be worn on the human body, the exosuit including a plurality of sensors, a plurality of power layer segments that mimic musculature anatomy and movements of the human body, communications circuitry, and control circuitry coupled to the communications circuitry, the plurality of sensors, and the power layer segments. The control circuitry is operative to monitor the plurality of sensors while a user of the exosuit is performing an exercise movement to obtain movement factors, analyze the movement factors to determine whether the user is performing the exercise movement within parameters associated with the exercise movement, and selectively activate and deactivate at least one of the plurality of actuators to provide spot assistance to the user in response to a determination that that user is not performing the exercise movement within the parameters associated with the exercise movement.

According to an embodiment, wherein the spot assistance enable the user to complete the exercise movement.

According to an embodiment, each of the plurality of power layer segments includes a flexdrive subsystem that is secured to a first load distribution member, a twisted string coupled to the flexdrive subsystem and secured to a second load distribution member, and power/communication lines coupled to the flexdrive subsystem.

An exercise assistance system for use on a human body is provided in an embodiment. The system can include an exosuit configured to be worn on the human body as a garment, the exosuit including a plurality of sensors, a plurality of power layer segments that mimic musculature anatomy and movements of the human body, communications circuitry, and control circuitry coupled to the communications circuitry, the plurality of sensors, and the power layer segments. The control circuitry is operative to determine a fitness level of a user wearing the exosuit, wherein the fitness level is less than a desired fitness level; and activate at least one of the plurality of power layer segments such that a fitness improving resistance level is exerted by the exosuit onto the user in a manner that results in an improvement of the fitness level of the user over time.

According to an embodiment, the fitness improving resistance level is such that a perceived level of effort is nearly imperceptible, yet results in an improvement of the fitness level of the user over time.

According to an embodiment, the fitness improving resistance level is such that the user is intermittently subjected to resistance during user movement activity.

According to an embodiment, the control circuitry is operative to access a database comprising fitness metrics associated with a user of the system, and adjust the fitness improving resistance level based on the fitness level and the fitness metrics.

According to an embodiment, the plurality of power layer segments each comprise at least one removable resistance element, wherein the at least one removable resistance element is replaceable with another removable resistance element.

An group exercise assistance system for use on a human body is provided in an embodiment. The system can include a first exosuit configured to be worn by a first person, the first exosuit including a plurality of sensor, a plurality of power layer segments that mimic musculature anatomy and movements of the human body, communications circuitry, and control circuitry coupled to the communications circuitry, the plurality of sensors, and the power layer segments. The control circuitry is operative to communicate with at least a second exosuit to obtain second suit movement data, wherein the second exosuit is worn by a second person, and activate at least one of the plurality of power layer segments to coordinate movements of the first exosuit with movements of the second exosuit based on the second suit movement data.

According to an embodiment, the second person is a group class instructor.

According to an embodiment, the control circuitry is operative to activate at least one of the plurality of power layer segments to coordinate movements of the first exosuit with movements of the second exosuit by applying exosuit enabled resistance to the first exosuit when the first person performs a coordinated movement.

According to an embodiment, the control circuitry is operative to handicap the first user by instructing the plurality of power layer segments to increase a resistance level of coordinated movements relative to a resistance level imposed on the second person.

An exercise assistance system for use on a human body is provided in an embodiment. The system can include an exosuit configured to be worn on the human body as a garment, the exosuit including a plurality of sensors, a plurality of power layer segments that mimic musculature anatomy and movements of the human body, communications circuitry, and control circuitry coupled to the communications circuitry, the plurality of sensors, and the power layer segments. The control circuitry is operative to monitor, via the plurality of sensors, movement of a user of the exosuit to obtain user data, wherein the user data comprises user movement and user response to changing forces, and adjust a resistance level of at least one of the power layer segments based on the user data.

According to an embodiment, the control circuitry is operative to generate an exercise program based on the user data, and selectively activate and deactivate at least one of the plurality of power layer segments based on the exercise program to apply exosuit enabled resistance to a user of the exosuit.

According to an embodiment, the control circuitry is operative to access a fitness test, selectively activate and deactivate at least one of the plurality of power layer segments based on the fitness test, and evaluate the user data obtained during the fitness test.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIGS. 1A-1C show front, back, and side views of a base layer of an exosuit according to an embodiment;

FIGS. 1D-1F show front, back, and side views, respectively, of a power layer according to an embodiment;

FIGS. 1G and 1H show respective front and back views of a human male's musculature anatomy;

FIGS. 1I and 1J show front and side views of illustrative exosuit having several power layer segments that approximate many of the muscles shown in FIGS. 1G and 1H, according to an embodiment;

DETAILED DESCRIPTION

Figure 2A:
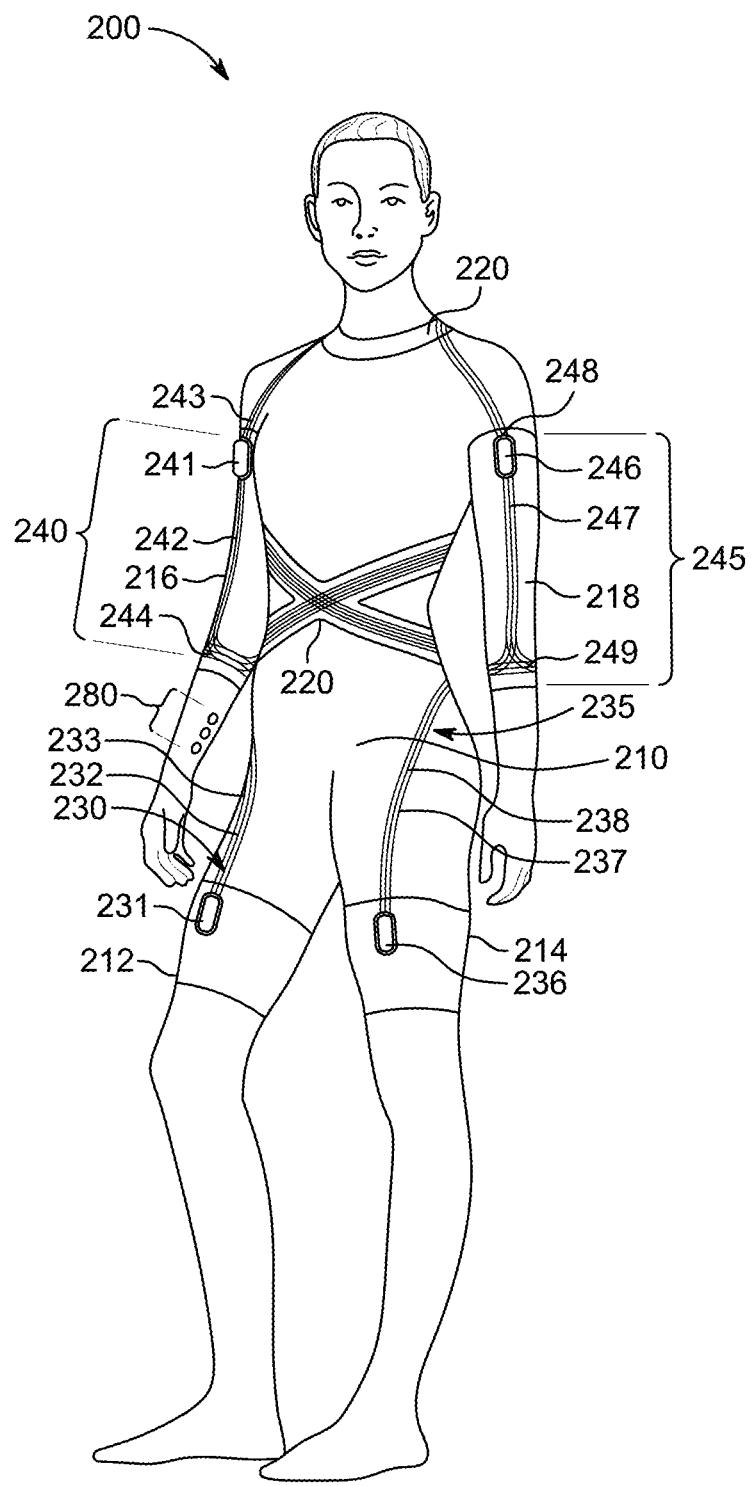
FIGS. 2A and 2B show front and back view of illustrative exosuit according to an embodiment.

In the following description, numerous specific details are set forth regarding the systems, methods and media of the disclosed subject matter and the environment in which such systems, methods and media may operate, etc., in order to provide a thorough understanding of the disclosed subject matter. It can be apparent to one skilled in the art, however, that the disclosed subject matter may be practiced without such specific details, and that certain features, which are well known in the art, are not described in detail in order to avoid complication of the disclosed subject matter. In addition, it can be understood that the examples provided below are exemplary, and that it is contemplated that there are other systems, methods and media that are within the scope of the disclosed subject matter.

In the descriptions that follow, an exosuit or assistive exosuit is a suit that is worn by a wearer on the outside of his or her body. It may be worn under the wearer's normal clothing, over their clothing, between layers of clothing, or may be the wearer's primary clothing itself. The exosuit may be assistive, as it physically assists the wearer in performing particular activities, or can provide other functionality such as communication to the wearer through physical expressions to the body, engagement of the environment, or capturing of information from the wearer. In some embodiments, an powered exosuit system can include several subsystems, or layers. In some embodiments, the powered exosuit system can include more or less subsystems or layers. The subsystems or layers can include the base layer, stability layer, power layer, sensor and controls layer, a covering layer, and user interface/user experience (UI/UX) layer.

The base layer provides the interfaces between the exosuit system and the wearer's body. The base layer may be adapted to be worn directly against the wearer's skin, between undergarments and outer layers of clothing, over outer layers of clothing or a combination thereof, or the base layer may be designed to be worn as primary clothing itself. In some embodiments, the base layer can be adapted to be both comfortable and unobtrusive, as well as to comfortably and efficiently transmit loads from the stability layer and power layer to the wearer's body in order to provide the desired assistance. The base layer can typically comprise several different material types to achieve these purposes. Elastic materials may provide compliance to conform to the wearer's body and allow for ranges of movement. The innermost layer is typically adapted to grip the wearer's skin, undergarments or clothing so that the base layer does not slip as loads are applied. Substantially inextensible materials may be used to transfer loads from the stability layer and power layer to the wearer's body. These materials may be substantially inextensible in one axis, yet flexible or extensible in other axes such that the load transmission is along preferred paths. The load transmission paths may be optimized to distribute the loads across regions of the wearer's body to minimize the forces felt by the wearer, while providing efficient load transfer with minimal loss and not causing the base layer to slip. Collectively, this load transmission configuration within the base layer may be referred to as a load distribution member. Load distribution members refer to flexible elements that distribute loads across a region of the wearer's body. Examples of load distribution members can be found in International Application PCT/US16/19565, titled "Flexgrip," the contents of which are incorporated herein by reference.

The load distribution members may incorporate one or more catenary curves to distribute loads across the wearer's body. Multiple load distribution members or catenary curves may be joined with pivot points, such that as loads are applied to the structure, the arrangement of the load distribution members pivots tightens or constricts on the body to increase the gripping strength. Compressive elements such as battens, rods, or stays may be used to transfer loads to different areas of the base layer for comfort or structural purposes. For example, a power layer component may terminate in the middle back due to its size and orientation requirements, however the load distribution members that anchor the power layer component may reside on the lower back. In this case, one or more compressive elements may transfer the load from the power layer component at the middle back to the load distribution member at the lower back.

The load distribution members may be constructed using multiple fabrication and textile application techniques. For example, the load distribution member can be constructed from a layered woven 45°/90° with bonded edge, spandex tooth, organza (poly) woven 45°/90° with bonded edge, organza (cotton/silk) woven 45°/90°, and Tyvek (non-woven). The load distribution member may be constructed using knit and lacing or horse hair and spandex tooth. The load distribution member may be constructed using channels and/or laces.

The base layer may include a flexible underlayer that is constructed to compress against a portion of the wearer's body, either directly to the skin, or to a clothing layer, and also provides a relatively high grip surface for one or more load distribution members to attach thereto. The load distribution members can be coupled to the underlayer to facilitate transmission of shears or other forces from the members, via the flexible underlayer, to skin of a body segment or to clothing worn over the body segment, to maintain the trajectories of the members relative to such a body segment, or to provide some other functionality. Such a flexible underlayer could have a flexibility and/or compliance that differs from that of the member (e.g., that is less than that of the members, at least in a direction along the members), such that the member can transmit forces along their length and evenly distribute shear forces and/or pressures, via the flexible underlayer, to skin of a body segment to which a flexible body harness is mounted.

Further, such a flexible underlayer can be configured to provide additional functionality. The material of the flexible underlayer could include anti-bacterial, anti-fungal, or other agents (e.g., silver nanoparticles) to prevent the growth of microorganisms. The flexible underlayer can be configured to manage the transport of heat and/or moisture (e.g., sweat) from a wearer to improve the comfort and efficiency of activity of the wearer. The flexible underlayer can include straps, seams, hook-and-loop fasteners, clasps, zippers, or other elements configured to maintain a specified relationship between elements of the load distribution members and aspects of a wearer's anatomy. The underlayer can additionally increase the ease with which a wearer can don and/or doff the flexible body harness and/or a system (e.g., a flexible exosuit system) or garment that includes the flexible body harness. The underlayer can additionally be configured to protect the wearer from ballistic weapons, sharp edges, shrapnel, or other environmental hazards (by including, e.g., panels or flexible elements of para-aramid or other high-strength materials). The flexible underlayer can also incorporate sensors that provide information on the pressure, temperature, size and fit, or other aspects of the skin and underlayer relative to its performance and the comfort and experience of the wearer. The load distribution members can also incorporate motors within the structure of the member that can be used to adjust the pressure and other characteristics of the load distribution member independently of the flexdrive forces.

The base layer can additionally include features such as size adjustments, openings and electro-mechanical integration features to improve ease of use and comfort for the wearer.

Size adjustment features permit the exosuit to be adjusted to the wearer's body. The size adjustments may allow the suit to be tightened or loosened about the length or circumference of the torso or limbs. The adjustments may comprise lacing, the Boa system, webbing, elastic, hook-and-loop or other fasteners. Size adjustment may be accomplished by the load distribution members themselves, as they constrict onto the wearer when loaded. In one example, the torso circumference may be tightened with corset-style lacing, the legs tightened with hook-and-loop in a double-back configuration, and the length and shoulder height adjusted with webbing and tension-lock fasteners such as cam-locks, D-rings or the like. The size adjustment features in the base layer may be actuated by the power layer to dynamically adjust the base layer to the wearer's body in different positions, in order to maintain consistent pressure and comfort for the wearer. For example, the base layer may be required to tighten on the thighs when standing, and loosen when sitting such that the base layer does not excessively constrict the thighs when seated. The dynamic size adjustment may be controlled by the sensor and controls layer, for example by detecting pressures or forces in the base layer and actuating the power layer to consistently attain the desired force or pressure, either through the flexdrive or through the motors in the load distribution members. This feature does not necessarily cause the suit to provide physical assistance, but can create a more comfortable experience for the wearer, or allow the physical assistance elements of the suit to perform better or differently depending on the purpose of the movement assistance.

Opening features in the base layer may be provided to facilitate donning (putting the exosuit on) and doffing (taking the exosuit off) for the wearer. Opening features may comprise zippers, hook-and-loop, snaps, buttons or other textile fasteners. In one example, a front, central zipper provides an opening feature for the torso, while hook-and-loop fasteners provide opening features for the legs and shoulders. In this case, the hook-and-loop fasteners provide both opening and adjustment features. In other examples, the exosuit may simply have large openings, for example around the arms or neck, and elastic panels that allow the suit to be donned and doffed without specific closure mechanisms. A truncated load distribution member may be simply extended to tighten on the wearer's body. Openings may be provided to facilitate toileting so the user can keep the exosuit on, but only have to remove or open a relatively small portion to use the bathroom.

Electro-mechanical integration features attach components of the stability layer, power layer and sensor and controls layer into the base layer for integration into the exosuit. The integration features may be for mechanical, structural, comfort, protective or cosmetic purposes. Structural integration features anchor components of the other layers to the base layer. For the stability and power layers, the structural integration features provide for load-transmission to the base layer and load distribution members, and may accommodate specific degrees of freedom at the attachment point. For example, a snap or rivet anchoring a stability or power layer element may provide both load transmission to the base layer, as well as a pivoting degree of freedom. Stitched, adhesive, or bonded anchors may provide load transmission with or without the pivoting degree of freedom. A sliding anchor, for example along a sleeve or rail, may provide a translational degree of freedom. Anchors may be separable, such as with snaps, buckles, clasps or hooks; or may be inseparable, such as with stitching, adhesives or other bonding. Size adjustment features as described above may allow adjustment and customization of the stability and power layers, for example to adjust the tension of spring or elastic elements in the passive layer, or to adjust the length of actuators in the power layer.

Other integration features such as loops, pockets, and mounting hardware may simply provide attachment to components that do not have significant load transmission requirements, such as batteries, circuit boards, sensors, or cables. In some cases, components may be directly integrated into textile components of the base layer. For example, cables or connectors may include conductive elements that are directly woven, bonded or otherwise integrated into the base layer.

Electromechanical integration features may also protect or cosmetically hide components of the stability, power or sensor and controls layers. Elements of the stability layer (e.g. elastic bands or springs), power layer (e.g. flexible linear actuators or twisted string actuators) or sensor and controls layer (e.g. cables) may travel through sleeves, tubes, or channels integrated into the base layer, which can both conceal and protect these components. The sleeves, tubes, or channels may also permit motion of the component, for example during actuation of a power layer element. The sleeves, channels, or tubes may comprise resistance to collapse, ensuring that the component remains free and uninhibited within.

Enclosures, padding, fabric coverings, or the like may be used to further integrate components of other layers into the base layer for cosmetic, comfort, or protective purposes. For example, components such as motors, batteries, cables, or circuit boards may be housed within an enclosure, fully or partially covered or surrounded in padded material such that the components do not cause discomfort to the wearer, are visually unobtrusive and integrated into the exosuit, and are protected from the environment. Opening and closing features may additionally provide access to these components for service, removal, or replacement.

In some cases—particularly for exosuits configurable for either provisional use or testing—a tether may allow for some electronic and mechanical components to be housed off the suit. In one example, electronics such as circuit boards and batteries may be over-sized, to allow for added configurability or data capture. If the large size of these components makes it undesirable to mount them on the exosuit, they could be located separately from the suit and connected via a physical or wireless tether. Larger, over-powered motors may be attached to the suit via flexible drive linkages that allow actuation of the power layer without requiring large motors to be attached to the suit. Such over-powered configurations allow optimization of exosuit parameters without constraints requiring all components to be attached or integrated into the exosuit.

Electro-mechanical integration features may also include wireless communication. For example, one or more power layer components may be placed at different locations on the exosuit. Rather than utilizing physical electrical connections to the sensors and controls layer, the sensor and controls layer may communicate with the one or more power layer components via wireless communication protocols such as Bluetooth, ZigBee, ultrawide band, or any other suitable communication protocol. This may reduce the electrical interconnections required within the suit. Each of the one or more power layer components may additionally incorporate a local battery such that each power layer component or group of power layer components are independently powered units that do not require direct electrical interconnections to other areas of the exosuit.

The stability layer provides passive mechanical stability and assistance to the wearer. The stability layer comprises one or more passive (non-powered) spring or elastic elements that generate forces or store energy to provide stability or assistance to the wearer. An elastic element can have an un-deformed, least-energy state. Deformation, e.g. elongation, of the elastic element stores energy and generates a force oriented to return the elastic element toward its least-energy state. For example, elastic elements approximating hip flexors and hip extensors may provide stability to the wearer in a standing position. As the wearer deviates from the standing position, the elastic elements are deformed, generating forces that stabilize the wearer and assist maintaining the standing position. In another example, as a wearer moves from a standing to seated posture, energy is stored in one or more elastic elements, generating a restorative force to assist the wearer when moving from the seated to standing position. Similar passive, elastic elements may be adapted to the torso or other areas of the limbs to provide positional stability or assistance moving to a position where the elastic elements are in their least-energy state.

Elastic elements of the stability layer may be integrated to parts of the base layer or be an integral part of the base layer. For example elastic fabrics containing spandex or similar materials may serve as a combination base/stability layer. Elastic elements may also include discrete components such as springs or segments of elastic material such as silicone or elastic webbing, anchored to the base layer for load transmission at discrete points, as described above.

The stability layer may be adjusted as described above, both to adapt to the wearer's size and individual anatomy, as well as to achieve a desired amount of pre-tension or slack in components of the stability layer in specific positions. For example, some wearers may prefer more pre-tension to provide additional stability in the standing posture, while others may prefer more slack, so that the passive layer does not interfere with other activities such as ambulation.

The stability layer may interface with the power layer to engage, disengage, or adjust the tension or slack in one or more elastic elements. In one example, when the wearer is in a standing position, the power layer may pre-tension one or more elastic elements of the stability layer to a desired amount for maintaining stability in that position. The pre-tension may be further adjusted by the power layer for different positions or activities. In some embodiments, the elastic elements of the stability layer should be able to generate at least 5 lbs force; preferably at least 50 lbs force when elongated.

The power layer can provide active, powered assistance to the wearer, as well as electromechanical clutching or locking to maintain components of the power or stability layers in a desired position or tension. The power layer can include one or more flexible linear actuators (FLA). An FLA is a powered actuator capable of generating a tensile force between two attachment points, over a given stroke length. An FLA is flexible, such that it can follow a contour, for example around a body surface, and therefore the forces at the attachment points are not necessarily aligned. In some embodiments, one or more FLAs can include one or more twisted string actuators. In the descriptions that follow, FLA refers to a flexible linear actuator that exerts a tensile force, contracts or shortens when actuated. The FLA may be used in conjunction with a mechanical clutch or lock that locks the tension force generated by the FLA in place so that the FLA motor does not have to consume power to maintain the desired tension force. Examples of such mechanical clutches are discussed below. In some embodiments, FLAs can include one or more twisted string actuators or flexdrives, as described in further detail in U.S. Pat. No. 9,266,233, titled "Exosuit System," the contents of which are incorporated herein by reference. FLAs may also be used in connection with electrolaminate clutches, which are also described in the U.S. Pat. No. 9,266,233. The electrolaminate clutch (e.g., clutches configured to use electrostatic attraction to generate controllable forces between clutching elements) may provide power savings by locking a tension force without requiring the FLA to maintain the same force.

The FLA can also include an in line elastic element, such as a rubber tube, that may be stretched by the actuator to a length known to apply a force to the body through the load bearing element because the elastic properties of the rubber tube are known. Control of the stretching length of the rubber tube therefore controls the force applied to the body. Active control of the stretching distance can be used to create different types of experiences for the wearer of the system. The wearer can be asked to hold a posture as the tube is slowly stretched in order to facilitate resistance training. The measured force on the tube by a separate sensor can be used to control the length of stretching of the tube in order to maintain a constant or changing force according to an objective for the wearer. For instance, the wearer may be using the suit to create forces that are related to experiences in a video game, or VR/AR simulation.

The powered actuators, or FLAs, are arranged on the base layer, connecting different points on the body, to generate forces for assistance with various activities. The arrangement can often approximate the wearer's muscles, in order to naturally mimic and assist the wearer's own capabilities. For example, one or more FLAs may connect the back of the torso to the back of the legs, thus approximating the wearer's hip extensor muscles. Actuators approximating the hip extensors may assist with activities such as standing from a seated position, sitting from a standing position, walking, or lifting. Similarly, one or more actuators may be arranged approximating other muscle groups, such as the hip flexors, spinal extensors, abdominal muscles or muscles of the arms or legs.

The one or more FLAs approximating a group of muscles are capable of generating at least 10 lb over at least a ½ inch stroke length within 4 seconds. In some embodiments, one or more FLAs approximating a group of muscles may be capable of generating at least 250 lb. over a 6-inch stroke within ½ second. Multiple FLAs, arranged in series or parallel, may be used to approximate a single group of muscles, with the size, length, power, and strength of the FLAs optimized for the group of muscles and activities for which they are utilized.

The sensor and controls layer captures data from the suit and wearer, utilizes the sensor data and other commands to control the power layer based on the activity being performed, and provides suit and wearer data to the UX/UI layer for control and informational purposes.

Sensors such as encoders or potentiometers may measure the length and rotation of the FLAs, while force sensors measure the forces applied by the FLAs. Inertial measurement units (IMUs) measure and enable computation of kinematic data (positions, velocities and accelerations) of points on the suit and wearer. These data enable inverse dynamics calculations of kinetic information (forces, torques) of the suit and wearer. Electromyographic (EMG) sensors may detect the wearer's muscle activity in specific muscle groups. Electronic control systems (ECSs) on the suit may use parameters measured by the sensor layer to control the power layer. Data from the IMUs may indicate both the activity being performed, as well as the speed and intensity. For example, a pattern of IMU or EMG data may enable the ECS to detect that the wearer is walking at a specific pace. This information then enables the ECS, utilizing the sensor data, to control the power layer in order to provide the appropriate assistance to the wearer. Stretchable sensors may be used as a strain gauge to measure the strain of the elements in the stability layer, and thereby predict the forces in the elastic elements of the stability layer. Stretchable sensors may be embedded in the base layer or grip layer and used to measure the motion of the fabrics in the base layer and the motion of the body.

Data from the sensor layer may be further provided to the UX/UI layer, for feedback and information to the wearer, caregivers or service providers. The UX/UI layer includes the wearer's and others' interaction and experience with the exosuit system. This layer includes controls of the suit itself such as initiation of activities, as well as feedback to the wearer and caregivers. A retail or service experience may include steps of fitting, calibration, training and maintenance of the exosuit system. Other UX/UI features may include additional lifestyle features such as electronic security, identity protection and health status monitoring.

The assistive exosuit can have a user interface for the wearer to instruct the suit which activity is to be performed, as well as the timing of the activity. In one example, a user may manually instruct the exosuit to enter an activity mode via one or more buttons, a keypad, or a tethered device such as a mobile phone. In another example, the exosuit may detect initiation of an activity from the sensor and controls layer, as described previously. In yet another example, the user may speak a desired activity mode to the suit, which can interpret the spoken request to set the desired mode. The suit may be pre-programmed to perform the activity for a specific duration, until another command is received from the wearer, or until the suit detects that the wearer has ceased the activity. The suit may include cease activity features that, when activated, cause the suit to cease all activity. The cease activity features can take into account the motion being performed, and can disengage in a way that takes into account the user's position and motion, and safely returns the user to an unloaded state in a safe posture.

The exosuit may have a UX/UI controller that is defined as a node on another user device, such as a computer or mobile smart phone. The exosuit may also be the base for other accessories. For example, the exosuit may include a cell phone chip so that the suit may be capable of receiving both data and voice commands directly similar to a cell phone, and can communicate information and voice signals through such a node. The exosuit control architecture can be configured to allow for other devices to be added as accessories to the exosuit. For example, a video screen may be connected to the exosuit to show images that are related to the use of the suit. The exosuit may be used to interact with smart household devices such as door locks or can be used to turn on smart televisions and adjust channels and other settings. In these modes, the physical assist of the suit can be used to augment or create physical or haptic experiences for the wearer that are related to communication with these devices. For instance, an email could have a pat on the back as a form of physical emoji that when inserted in the email causes the suit to physically tap the wearer or perform some other type of physical expression to the user that adds emphasis to the written email.

The exosuit may provide visual, audio, or haptic feedback or cues to inform the user of various exosuit operations. For example, the exosuit may include vibration motors to provide haptic feedback. As a specific example, two haptic motors may be positioned near the front hip bones to inform the user of suit activity when performing a sit-to-stand assistive movement. In addition, two haptic motors may be positioned near the back hip bones to inform the user of suit activity when performing a stand-to-sit assistive movement. The exosuit may include one or more light emitting diodes (LEDs) to provide visual feedback or cues. For example, LEDS may be placed near the left and/or right shoulders within the peripheral vision of the user. The exosuit may include a speaker or buzzer to provide audio feedback or cues.

In other instances, the interaction of the FLA's with the body through the body harness and otherwise can be used as a form of haptic feedback to the wearer, where changes in the timing of the contraction of the FLA's can indicate certain information to the wearer. For instance, the number or strength of tugs of the FLA on the waist could indicate the amount of battery life remaining or that the suit has entered a ready state for an impending motion.

The control of the exosuit may also be linked to the sensors that are measuring the movement of the wearer, or other sensors, for instance on the suit of another person, or sensors in the environment. The motor commands described herein may all be activated or modified by this sensor information. In this example, the suit can exhibit its own reflexes such that the wearer, through intentional or unintentional motions, cues the motion profile of the suit. When sitting, for further example, the physical movement of leaning forward in the chair, as if to indicate an intention to stand up, can be sensed by the suit IMU's and be used to trigger the sit to stand motion profile. In one embodiment, the exosuit may include sensors (e.g., electroencephalograph (EEG) sensor) that are able to monitor brain activity may be used to detect a user's desire to perform a particular movement. For example, if the user is sitting down, the EEG sensor may sense the user's desire to stand up and cause the exosuit to prime itself to assist the user in a sit-to-stand assistive movement.

The suit may make sounds or provide other feedback, for instance through quick movements of the motors, as information to the user that the suit has received a command or to describe to the user that a particular motion profile can be applied. In the above reflex control example, the suit may provide a high pitch sound and/or a vibration to the wearer to indicate that it is about to start the movement. This information can help the user to be ready for the suit movements, improving performance and safety. Many types of cues are possible for all movements of the suit.

Control of the suit includes the use of machine learning techniques to measure movement performance across many instances of one or of many wearers of suits connected via the internet, where the calculation of the best control motion for optimizing performance and improving safety for any one user is based on the aggregate information in all or a subset of the wearers of the suit. The machine learning techniques can be used to provide user specific customization for exosuit assistive movements. For example, a particular user may have an abnormal gait (e.g., due to a car accident) and thus is unable to take even strides. The machine learning may detect this abnormal gait and compensate accordingly for it.

FIGS. 1A-1C show front, back, and side views of a base layer 100 of an exosuit according to an embodiment. Base layer 100 may be worn as a single piece or as a multiple pieces. As shown, base layer 100 is shown to represent multiple pieces that can serve as load distribution members (LDMs) for the power layer (shown in FIGS. 1D-1F). Base layer 100 and any LDMs thereof can cover or occupy any part of the human body as desired. The LDMs shown in FIGS. 1A-1C are merely illustrative of a few potential locations and it should be appreciated that additional LDMs may be added or certain LDMs may be omitted.

Base layer 100 can include calf LDMs 102 and 104 that are secured around the calf region or lower leg portion of the human. Calf LDMs 102 and 104 are shown to be positioned between the knees and the ankles, but this is merely illustrative. If desired, calf LDM 102 and 104 can also cover the foot and ankle and/or the knee.

Base layer 100 can include thigh LDMs 106 and 108 that are secured around the thigh region of the human. Thigh LDMs 106 and 108 are shown to be positioned between the knees and an upper region of the thighs. In some embodiments, thigh LDMs 106 and 108 and calf LDMs 102 and 104, respectively, may be merged together to form leg LDMs that cover the entirety of the legs and/or feet.

Base layer 100 can include hip LDM 110 that is secured around a hip region of the human. LDM 110 may be bounded such that it remains positioned above the toileting regions of the human. Such bounding may make toileting relatively easy for the human as he or she would be not be required to remove base layer 100 to use the bathroom. In some embodiments, LDM 110 may be attached to thigh LDMs 106 and 108, but the toileting regions may remain uncovered. In another embodiment, a removable base layer portion may exist between LDM 100 and thigh LDMS 106 and 108.

Base layer 100 can include upper torso LDM 112 that secured around an upper torso region of the human. Upper torso LDM 112 may include waist LDM 113, back LDM 114, shoulder LDM 115, and shoulder strap LDMs 116. Waist LDM 113, back LDM 114, shoulder LDM 115, and shoulder strap LDMs 116 may be integrally formed to yield upper torso LDM 112. In some embodiments, a chest LDM (not shown) may also be integrated into upper torso LDM 112. Female specific exosuits may have built in bust support for the chest LDM.

Base layer 100 can include upper arm LDMs 120 and 122 and lower arm LDMs 124 and 126. Upper arm LDMs 120 and 122 may be secured around bicep/triceps region of the arm and can occupy space between the shoulder and the elbow. Lower arm LDMs 124 and 126 may be secured around the forearm region of the arm and can occupy the space between the elbow and the wrist. If desired, upper arm LDM 120 and lower arm LDM 124 may be integrated to form an arm LDM, and upper arm LDM 122 and lower arm LDM 126 may be integrated to form another arm LDM. In some embodiments, arm LDMS 120, 122, 124, and 126 may form part of upper torso LDM 112.

Base layer 100 can include gluteal/pelvic LDM 128 that is secured the gluteal and pelvic region of the human. LDM 128 may be positioned between thigh LDMs 106 and 108 and hip LDM 110. LDM 128 may have removable portions such as buttoned or zippered flaps that permit toileting. Although not shown in FIGS. 1A-1C, LDMs may exist for the feet, toes, neck, head, hands, fingers, elbows, or any other suitable body part.

As explained above, the LDMs may serve as attachment points for components of the power layer. In particular, the components that provide muscle assistance movements typically need to be secured in at least two locations on the body. This way, when the flexible linear actuators are engaged, the contraction of the actuator can apply a force between the at least two locations on the body. With LDMs strategically placed around the body, the power layer can also be strategically placed thereon to provide any number of muscle assistance movements. For example, the power layer may be distributed across different LDMs or within different regions of the same LDM to approximate any number of different muscles or muscle groups. The power layer may approximate muscle groups such as the abdominals, adductors, dorsal muscles, shoulders, arm extensors, wrist extensors, gluteals, arm flexors, wrist flexors, scapulae fixers, thigh flexors, lumbar muscles, surae, pectorals, quadriceps, and trapezii.

FIGS. 1D-1F show front, back, and side views, respectively, of a power layer according to an embodiment. The power layer is shown as multiple segments distributed across and within the various LDMs. As shown, the power layer can include power layer segments 140-158. Each of power layer segments can include any number of flexible linear actuators. Some of the power layer segments may exist solely on the anterior side of the body, exist solely on the posterior side, start on the anterior side and wrap around to the posterior side, start on the posterior side and wrap around to the anterior side, or wrap completely around a portion of the body. Power layer segment (PLS) 140 may be secured to LDM 102 and LDM 106, and PLS 141 may be secured to LDM 104 and LDM 108. PLS 142 may be secured to LDM 106 and LDM 110 and/or LDM 114, and PLS 143 may be secured to LDM 108 and LDM 110 and/or LDM 114. PLS 145 may be secured to LDM 110 and LDM 113 and/or to LDM 114 or LDM 128. PLS 146 may be secured to LDM 115 and LDM 120, and PLS 147 may be secured to LDM 115 and LDM 122. PLS 148 may be secured to LDM 120 and LDM 124, and PLS 149 may be secured to LDM 122 and LDM 126.

PLS 150 may be secured to LDM 104 and LDM 108, and PLS 151 may be secured to LDM 102 and LDM 106. PLS 152 may be secured to LDM 106 and LDM 110 and/or to LDM 113, and PLS 153 may be secured to LDM 108 and LDM 110 and/or LDM 113. PLS 154 may be secured to LDM 112 and LDM 110. PLS 155 may be secured to LDM 112 and LDM 120, and PLS 156 may be secured to LDM 112 and LDM 122. PLS 157 may be secured to LDM 120 and LDM 124, and PLS 158 may be secured to LDM 122 and LDM 126.

It should be appreciated that the power layer segments are merely illustrative and that additional power layer segments may be added or that some segments may be omitted. In addition, the attachment points for the power layer segments are merely illustrative and that other attachment points may be used. The human body has many muscles, including large and small muscles that are arranged in all sorts of different configuration. For example, FIGS. 1G and 1H show respective front and back views of a human male's musculature anatomy, which shows many muscles. In particular, the abdominals, adductors, dorsal muscles, shoulders, arm extensors, wrist extensors, gluteals, arm flexors, wrist flexors, scapulae fixers, thigh flexors, lumbar muscles, pectorals, quadriceps, and trapezii are all shown.

FIGS. 1I and 1J show front and side views of illustrative exosuit 170 having several power layer segments that approximate many of the muscles shown in FIGS. 1G and 1H. The power layer segments are represented by the individual lines that span different parts of the body. These lines may represent specific flexible linear actuators or groups thereof that work together to form the power layer segments that are secured to the LDMs (not shown). As shown, the FLAs may be arrayed to replicate at least a portion of each of the abdominal muscles, dorsal muscles, shoulder muscles, arm extensor and flexor muscles, gluteal muscles, quadriceps muscles, thigh flexor muscles, and trapezii muscles. Thus, exosuit 170 exemplifies one of many possible different power layer segment arrangements that may be used in exosuits in accordance with embodiments discussed herein. Other possible power layer segment arrangements are illustrated and discussed below.

The power layer segments may be arranged such that they include opposing pairs or groups, similar to the way human muscles are arranged in opposing pairs or groups of muscles. That is, for a particular movement, the opposing pairs or groups can include protagonist and antagonist muscles. While performing the movement, protagonist muscles may perform the work, whereas the antagonist muscles provide stabilization and resistance to the movement. As a specific example, when a user is performing a curl, the biceps muscles may serve as the protagonist muscles and the triceps muscles may serve as the antagonist muscles. In this example, the power layer segments of an exosuit may emulate the biceps and triceps. When the biceps human muscle is pulling to bend the elbow, the exosuit triceps power layer segment can pull on the other side of the joint to resist bending of the elbow by attempting to extend it. The power layer segment can be, for example, either be a FLA operating alone to apply the force and motion, or a FLA in series with an elastic element. In the latter case, the human biceps would be working against the elastic element, with the FLA adjusting the length and thereby the resistive force of the elastic element.

Thus, by arranging the power layer segments in protagonist and antagonist pairs, the power layers segments can mimic or emulate any protagonist and antagonist pairs of the human anatomy musculature system. This can be used to enable exosuits to provide assistive movements, alignment movements, and resistive movements. For example, for any exercise movement requires activation of protagonist muscles, a subset of the power layer segments can emulate activation of antagonist muscles associated with that exercise movement to provide resistance.

The design flexibility of the LDMs and PLSs can enable assist, resist, and align (ARA) exosuits to be constructed in accordance with embodiments discussed herein. Using ARA exosuits, the power layer segments can be used to resist motion, assist motion, or align the user's form. Resistive motion can be used to provide targeted workouts anywhere, without the need for extra gear or only requiring minimal gear. That is, the ARA exosuit can serve as a workout mechanism that the user can use in his or her home. The assistive motion can be used to provide the user with an additive boost to assist in maximizing training. Exosuit based alignment may provide audio, visual, or haptic cues for proprioceptive feedback to maintain proper form during an exercise movement.

ARA exosuits according to embodiments discussed herein can be used in wearable fitness applications and coaching applications. The ARA exosuit can help users build power by forcing them to work at higher speeds/demands or with higher forces. The ARA exosuit can provide proprioception improvements by enabling the user to learn skills faster and more accurately. In addition, the ARA suit can improve balance with posture feedback. The ARA exosuit can provide neural training, for example, by constantly challenging the muscles. The ARA exosuit can be used to provide high intensity training (HIT). For example, HIT can be performed by having the exosuit dynamically tune resistance over a range of motion or activity. The ARA exosuit can be used to ensure proper form is maintained even if the user is fatigued. The ARA exosuit can be used to provide cross-training or stretching. For example, the ARA exosuit can enforce a stretching routine that will improve performance. The exosuit can also monitor and track a user's flexibility, fitness, and performance gains. The exosuit can be used to analyze and cater to a person's training needs, including, for example, individual fitness goals, protection from re-injury, workout recovery, rehabilitation, injury, and maintaining fitness.

The ARA exosuit can be used in many different aspects related to fitness. For example, in some embodiments, the ARA exosuit can be used in connection with discrete exercise events. As a specific example, if the user is performing a squat movement, the suit can monitor the user during the squat event and provided feedback and/or assistance where needed. The exosuit can change resistance to provide guidance to the wearer for preferred movements in a dynamic way. This can include dynamic resistance change for motion training and not necessarily for just resistance or strength training.

In other embodiments, the ARA exosuit can assess the activity, fitness, or metabolic state of the user wearing the suit. For example, the suit can determine how fit a person is or determine how hard a person is exerting him or herself when performing a task. Based on these determinations, the suit can provide resistance, for example, as an attempt to encourage the user to achieve a certain level of fitness. For example, assume a user has a set of defined goals. The suit can, based in part of the goals, provide resistance throughout the day as a part of the user's everyday activity in such a way that the user does not have to participate in discrete exercise in order to achieve a certain level of fitness that comply with the set of defined goals. The resistance can be applied in a passive way that subtly increases the user's fitness without overwhelming the user. As a specific example, the suit can make an ordinary task such as walking more difficult (e.g., by applying resistance that approximates walking at a 15% grade). This way, the user is increasing his or her fitness as part of normal everyday life.

In yet another embodiment, the ARA exosuit can conduct various fitness tests on the user. For example, in one embodiment, the suit can conduct a stress test for heart health. The suit can monitor the user's vitals as it instructs the user to conduct the stress test. The suit can instruct the user to walk and can adjust the resistance to change the difficulty for the user to walk, thereby creating the stress condition. The suit can provide increasing or varying levels of resistance in a coordinated way and track how the wearer moves, and relate the data to a relative fitness level.

In yet another embodiment, the ARA exosuit can track and store all data related to the wearer's movement (e.g., motion data) and their response to changing forces (e.g., power data). The stored data can be used to create custom exercise programs for the user, or to create status reports showing progress.

In other embodiments, the ARA exosuit can be used in a class environment. In the class environment, the exosuit may operate in conjunction with other exosuits to promote coordination among participants. Thus, the exosuits can collectively adjust their respective resistance levels to create a uniform class experience for all participants. In some embodiments, users that are more fit than other users may be required to exert more force to overcome resistance applied thereto by the suit. For example, some users may be handicapped by making certain movements more difficult so the relative effort exerted by participants is approximately even.

Figure 2B:
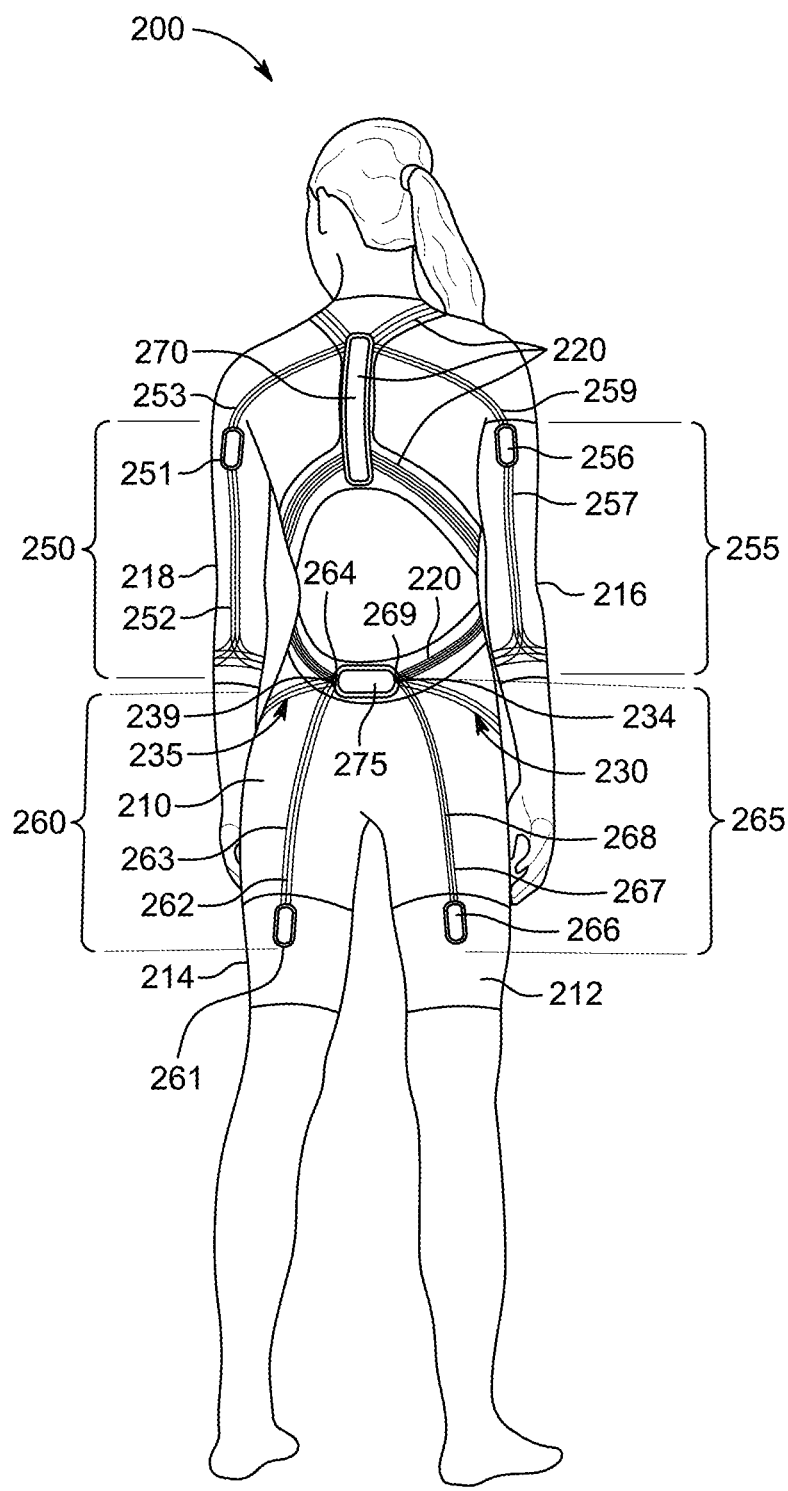

FIGS. 2A and 2B show front and back view of illustrative assist, resist, and align (ARA) exosuit 200 according to an embodiment. Exosuit 200 may embody some or all of the base layer, stability layer, power layer, sensor and controls layer, a covering layer, and user interface/user experience (UI/UX) layer, as discussed above. In addition, ARA exosuit 200 may represent one of many different specification implementations of the exosuit shown in FIGS. 1A-IF. ARA exosuit 200 can include base layer 210 with thigh LDMs 212 and 214, arm LDMs 216 and 218, and upper torso LDM 202. Thigh LDMs 212 and 214 may wrap around the thigh region of the human, and arm LDMs 216 and 218 may wrap around arm region (including the elbow) of the human. Upper torso LDM 220 may wrap around the torso and neck of the human as shown. In particular, LDM 220 may cross near the abdomen, abut the sacrum, cover a portion of the back, and extend around the neck.

ARA exosuit 200 can include extensor PLSs 230 and 235 secured to thigh LDM 212 and 214 and upper torso LDM 220. Extensor PLSs 230 and 235 may provide leg muscle extensor ARA movements. Extensor PLS 230 may include flexdrive subsystem 231, twisted string 232, and power/communication lines 233. Flexdrive subsystem 231 may include a motor, sensors, a battery, communications circuitry, and/or control circuitry. Twisted string 232 may be attached to flexdrive subsystem 231 and an attachment point 234 on LDM 220. Power/communications lines 233 may convey control signals and/or power to flexdrive subsystem 231. Extensor PLS 235 may include flexdrive subsystem 236, twisted string 237, and power/communication lines 238. Twisted string 237 may be attached to flexdrive subsystem 236 and attachment point 239.

The power layer segments can include a resistance element that applies a variable amount of resistance, ranging between a zero resistance level to a maximum resistance level. The resistance elements can be replaceable such that different levels of resistance can be achieved. For example, if a first resistance element is not able to generate enough resistance, it may be replaced with a second resistance element that generates more resistance. In some examples, the resistance element can be varied in size such that different sizes can be used for different applications, body site location (e.g., arms, legs), and size of the persons. This way, modularity in resistance elements is provided that reduces cost and increases usefulness. The power layer segments may be able to sense stretching actions being performed by the user. For example, the power layer segment can include integrated stretch sensing, power conduits, and communications channels.

ARA exosuit 200 can include flexor PLSs 240 and 245 and extensor PLSs 250 and 255 that are secured to LDMs 216, 218, and 220 (as shown). Flexor PLSs 240 and 245 may provide arm muscle flexor ARA movements, and extensor PLSs 250 and 255 may provide arm muscle extensor ARA movements. Flexor PLS 240 may include flexdrive subsystem 241, twisted string 242, and power/communication lines 243. Twisted string 242 may be attached to flexdrive subsystem 241 and attachment point 244. Power/communication lines 243 may be coupled to power and communications module 270. Flexor PLS 245 may include flexdrive subsystem 246, twisted string 247, and power/communication lines 248. Twisted string 247 may be attached to flexdrive subsystem 246 and attachment point 249. Power/communication lines 248 may be coupled to power and communications module 270. Extensor PLS 250 may include flexdrive subsystem 251, twisted string 252, and power/communication lines 253. Twisted string 252 may be attached to flexdrive subsystem 251 and attachment point 254. Power/communication lines 253 may be coupled to power and communications module 270. Extensor PLS 250 may include flexdrive subsystem 256, twisted string 257, and power/communication lines 258. Twisted string 256 may be attached to flexdrive subsystem 256 and attachment point 259. Power/communication lines 258 may be coupled to power and communications module 270.

ARA exosuit 200 can include flexor PLS 260 and 265 that are secured to thigh LDMs 212 and 214 and LDM 220. Flexor PLSs 260 and 265 may provide leg muscle flexor ARA movements. Flexor PLS 260 may include flexdrive subsystem 261, twisted string 262, and power/communication lines 263. Twisted string 262 may be attached to flexdrive subsystem 261 and attachment point 264. Power/communication lines 263 may be coupled to power and communications module 275. Flexor PLS 266 may include flexdrive subsystem 266, twisted string 267, and power/communication lines 268. Twisted string 267 may be attached to flexdrive subsystem 266 and attachment point 269. Power/communication lines 263 may be coupled to power and communications module 275

ARA exosuit 200 is designed to assist, resist, and align movements being performed by the user of the suit. ARA exosuit 200 may include many sensors in various locations to provide data required by control circuitry to provide such movements. These sensors may be located anywhere on base layer 210 and be electrically coupled to power and communications lines (e.g., 233, 237, 243, 247, 253, 257, 263, 267, or other lines). The sensors may provide absolute position data, relative position data, accelerometer data, gyroscopic data, inertial moment data, strain gauge data, resistance data, or any other suitable data.

ARA exosuit 200 may include user interface 280 that enables the user to control the exosuit. For example, user interface 280 can include several buttons or a touch screen interface. User interface 280 may also include a microphone to receive user spoken commands User interface 280 may also include a speaker that can be used to playback voice recordings. Other user interface element such as buzzers (e.g., vibrating elements) may be strategically positioned around exosuit 200.

ARA exosuit 200 can include communications circuitry such as that contained in power and communications module 270 or 275 to communicate directly with a user device (e.g., a smartphone) or with the user device via a central sever. The user may use the user device to select one or more exercises he or she would like to perform, and upon selection of the one or more exercises, ARA exosuit 200 can the assist, resist, or align movement. The user device or exosuit 200 may provide real-time alignment guidance as to the user's performance of the movement, and exosuit 200 may provide resistance or assistance to the movement.

Figure 3A:
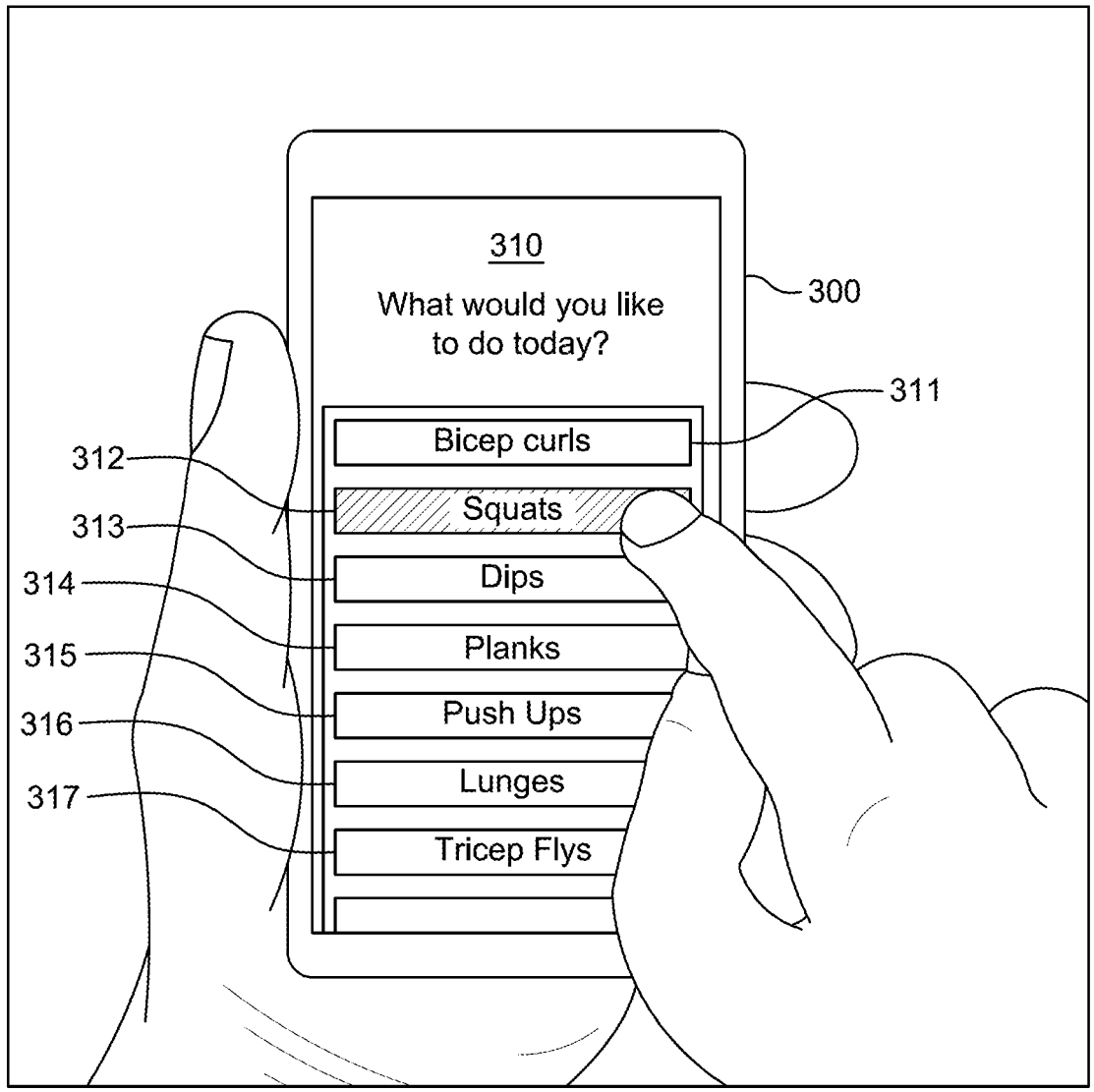
FIGS. 3A and 3B shows illustrative screen shots on a user device according to an embodiment.
Figure 3B:
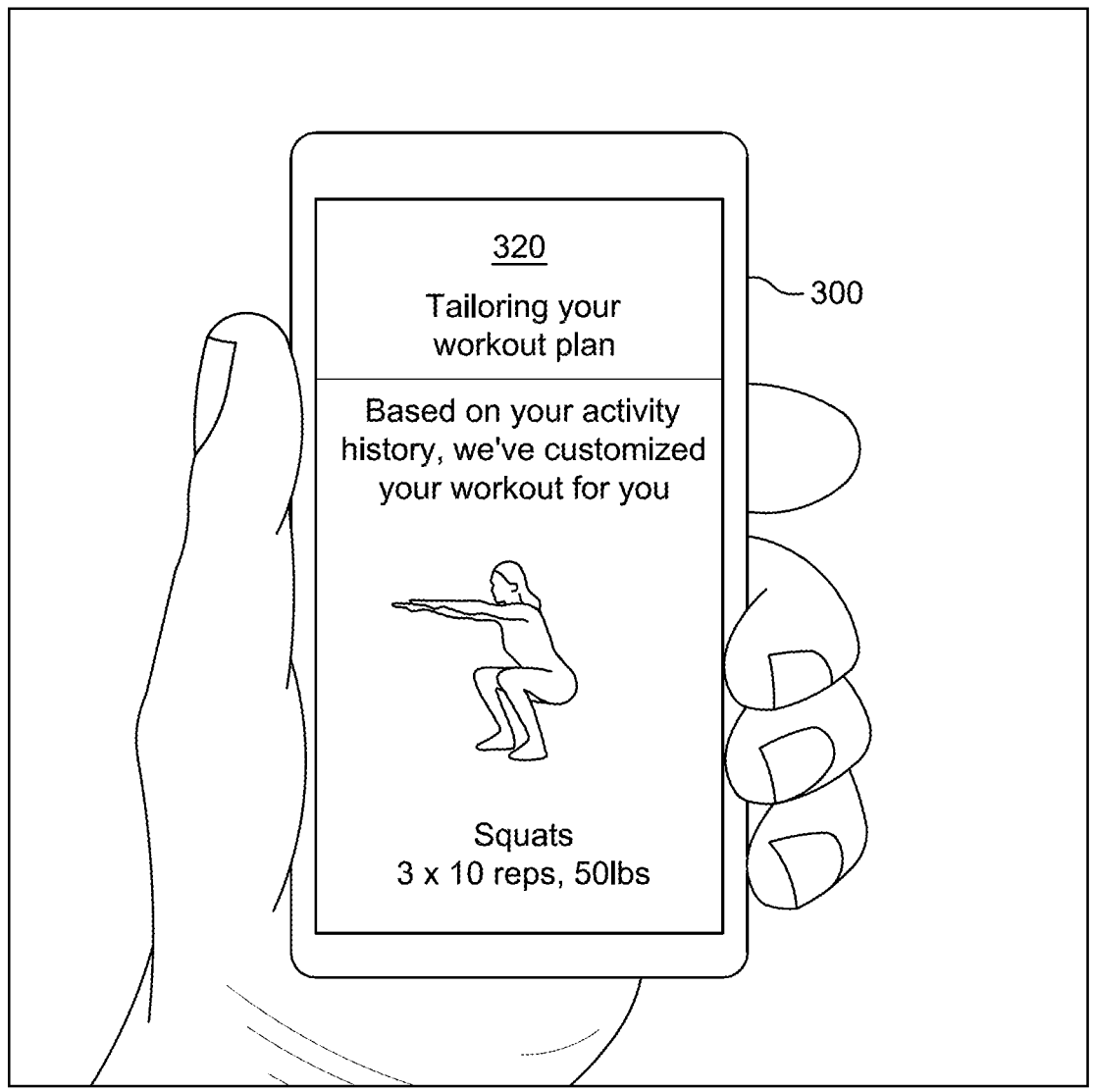

FIG. 3A shows an illustrative screen shot 310 on user device 300 according to an embodiment. Screen shot 310 includes several selectable exercise assets 311-317 that can be chosen by a user. Additional assets, not shown, may be scrolled to if desired. As shown, user has selected asset 312, which corresponds to a squat exercise. In response to the user selection of asset 312, screen shot 320 may be displayed on user device 300, as shown in FIG. 3B. Screen shot 320 may inform the user how many reps and sets of squats he or she should complete for the workout.

Figure 4A:
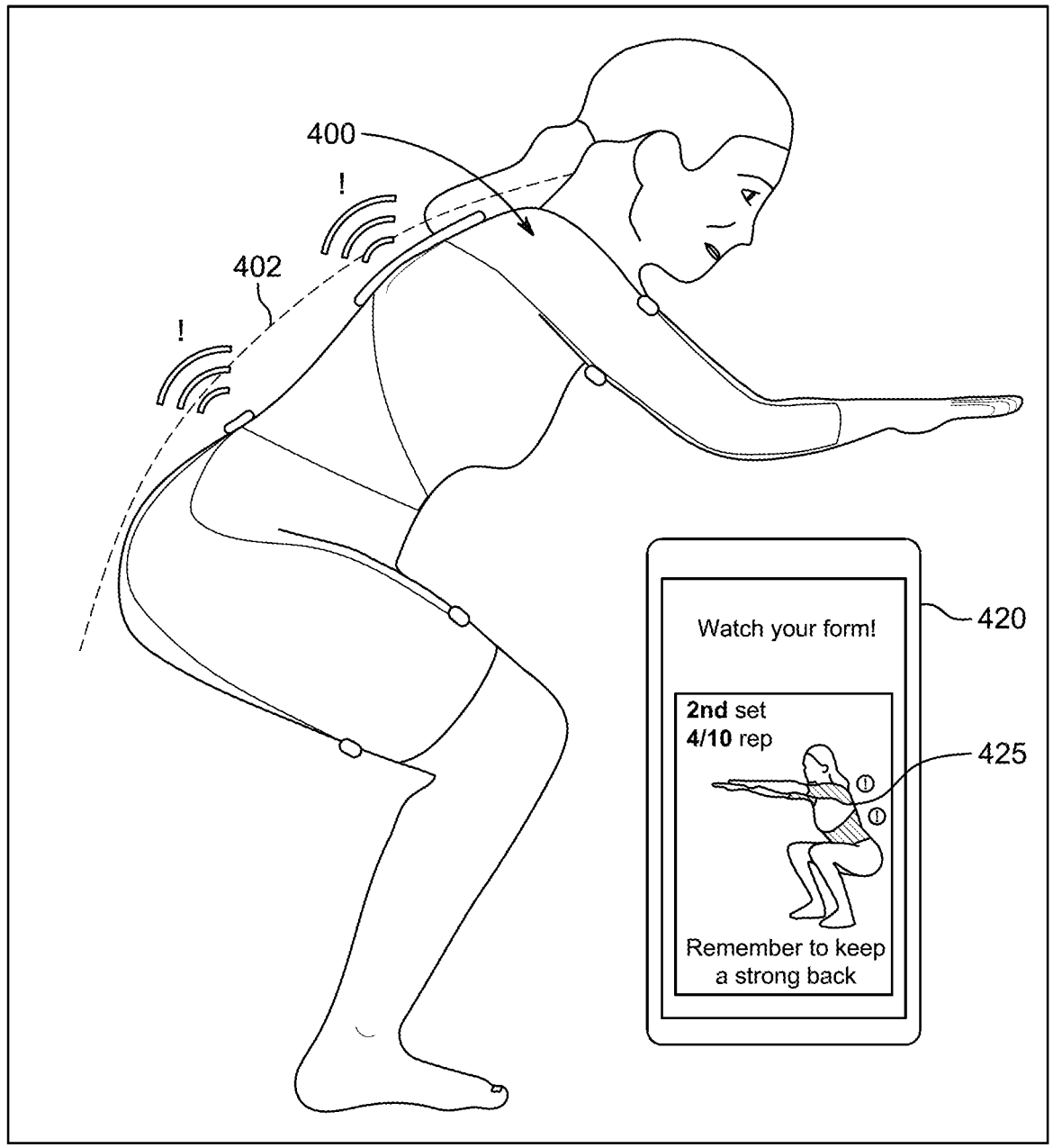
FIGS. 4A-4C show illustrative examples in which an ARA exosuit provides alignment guidance while the user performs an exercise, according to an embodiment.
Figure 4B:
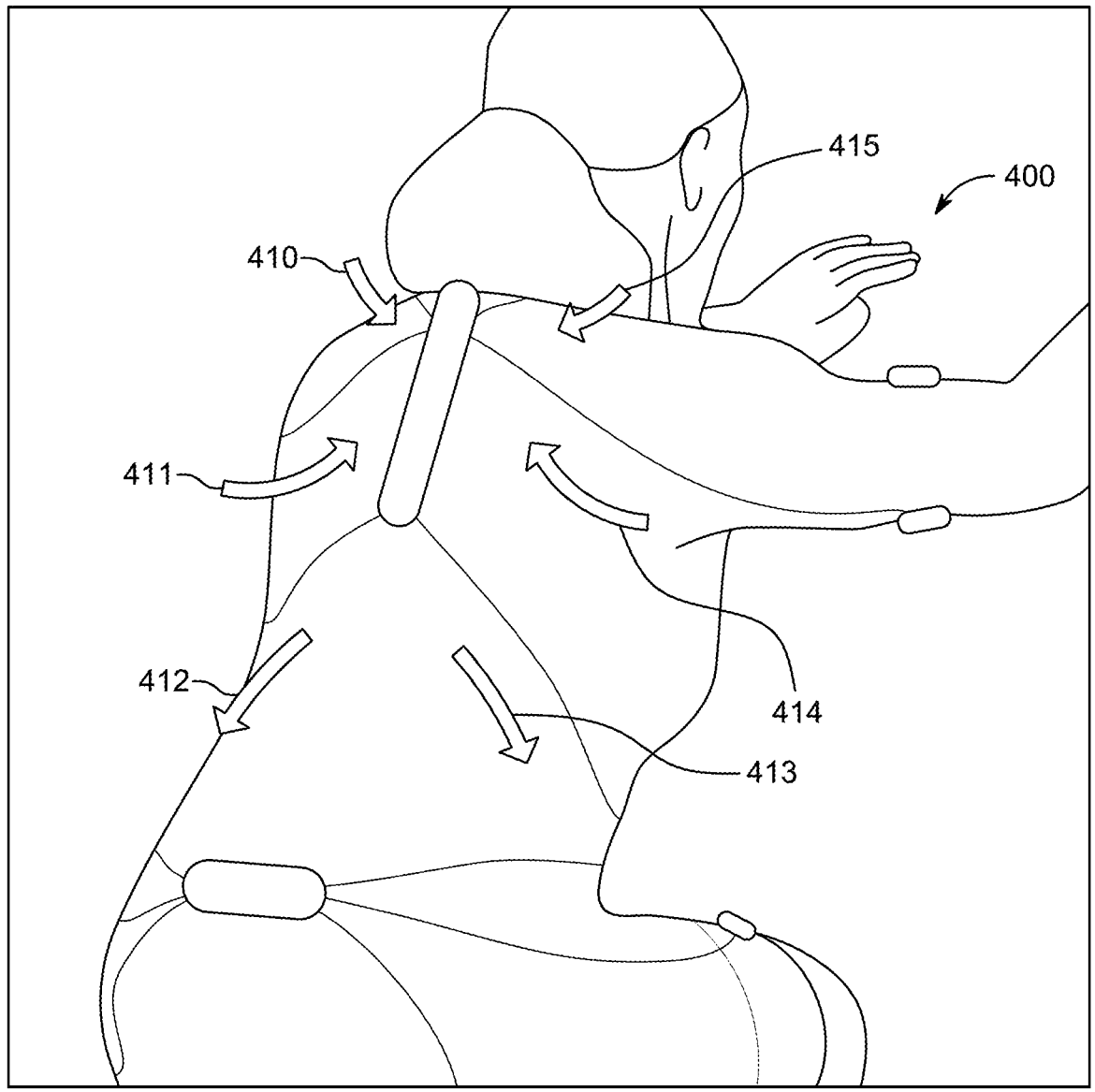
Figure 4C:
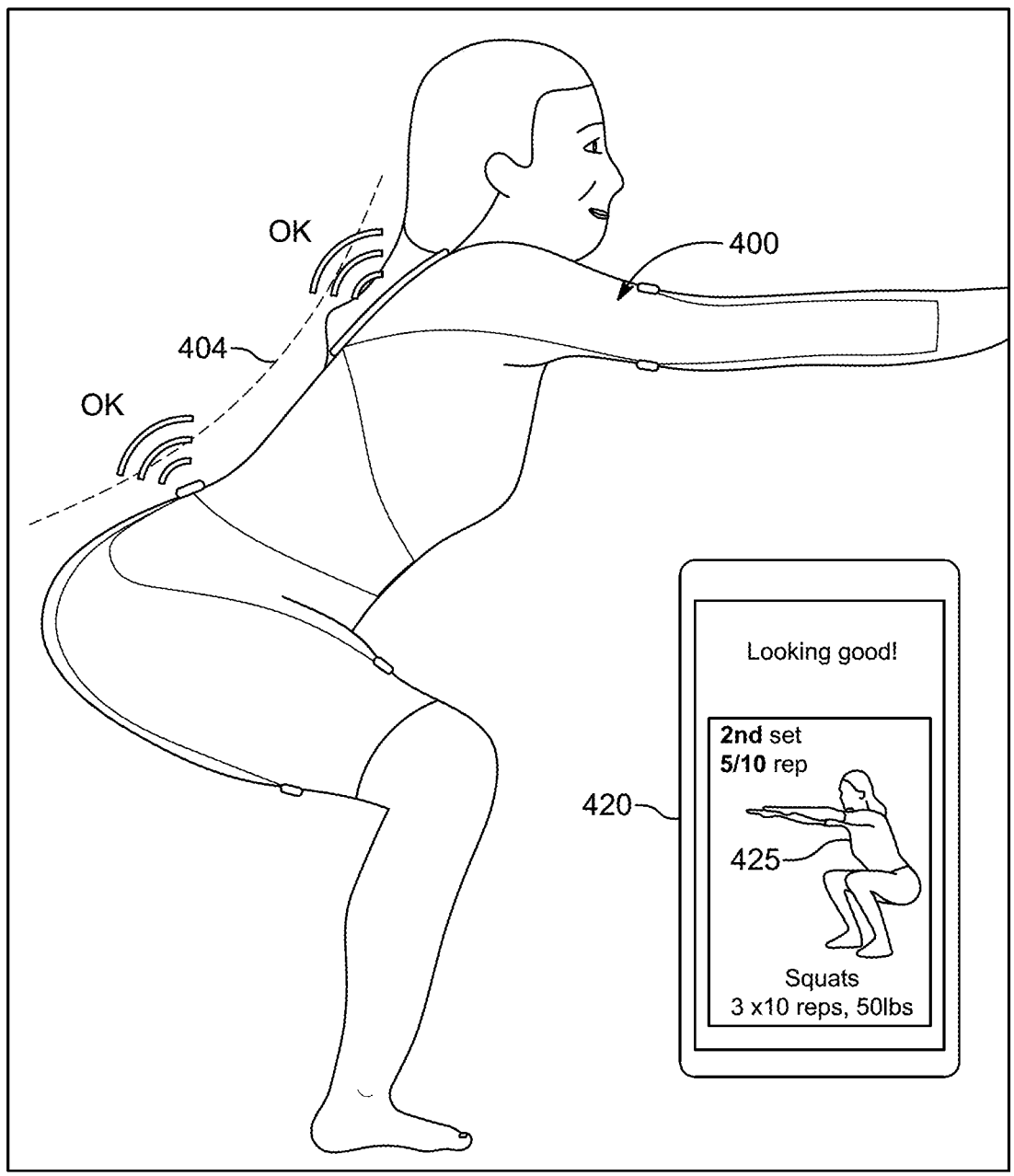

FIGS. 4A-4C show illustrative examples in which ARA exosuit 400 provides alignment guidance while the user performs an exercise. Alignment guidance may be provided in the form of an avatar 425 of the user on the screen of user device 420. Avatar 425 can emulate the form of the user while the user performing the movement. If the user's position is not correct, user device 420 may show region(s) on avatar 425 that are not aligned properly. In addition, exosuit 400 may provide cues if the user's form is not properly aligned. For example, exosuit 400 may provide audio, haptic, and/or visual cues that alignment is not proper and can indicate which regions require correction. In FIG. 4A, exosuit 400 may determine that there is excessive curvature 402 in the back of the user, and as a result, exosuit 400 or user device 420 may inform the user of the necessary corrective action to be taken to conform with proper alignment associated with the movement. The user device can be a smart phone, computer, laptop, tablet, or television.

In addition to or in the alternative to providing audio, haptic, and/or visual cues, ARA exosuit 400 may use one or more power layer segments to re-position the user in correct alignment in response to determining that the user is not in proper alignment. Selective activation of the appropriate power layer segments can provide proprioceptive feedback to the user to maintain proper form. Thus, when the user deviates from proper form, exosuit 400 can guide the user back to proper alignment.

FIG. 4B shows illustrative data input vectors 410-415 that are being detected by sensors located on exosuit 400. As illustrated, each of the data input vectors may be sensed on different regions of an upper torso LDM. These inputs can be fed to a processing unit located within exosuit 400 or can be transmitted to user device 425 (of FIG. 4A) so that calculations can be made as to whether the user is in proper alignment.

FIG. 4C shows that exosuit 400 has determined that proper curvature 404 exists in the user's back. As a result, exosuit 400 and/or user device 420 may provide encouraging feedback. For example, user device 420 may display a message stating "looking good" and can include other information such as how many reps have been completed for the set.

Figure 5:
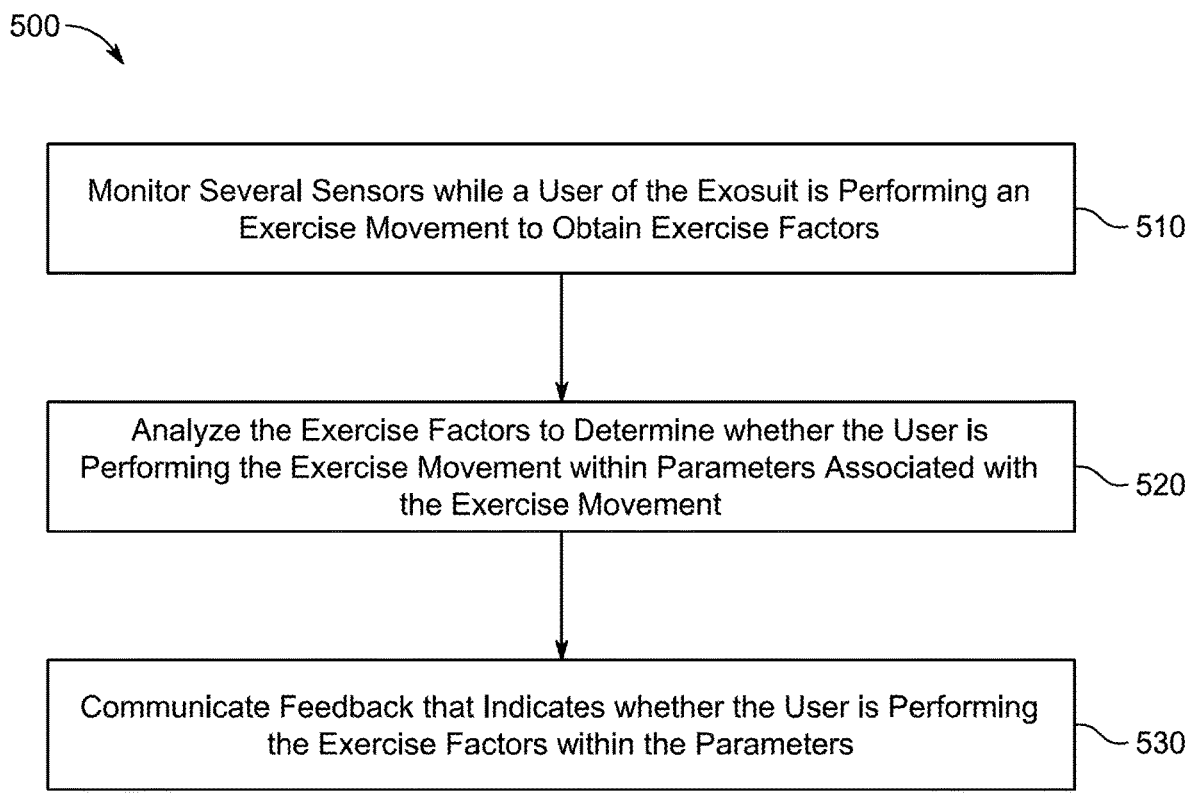
FIG. 5 shows an illustrative flowchart for providing alignment guidance using an exosuit according to an embodiment.

FIG. 5 shows an illustrative flowchart of process 500 for providing alignment guidance using an exosuit according to an embodiment. Process 500 may be implemented in an exosuit or in combination with an exosuit and a user device. The exosuit may embody the elements of exosuits discussed above such as in FIGS. 1A-1F and FIGS. 2A and 2B. The exosuit may include several sensors that are disposed throughout the suit and several power layer segments that mimic musculature anatomy movements of the human body. The exosuit may include communications circuitry and control circuitry coupled to the communications circuitry, the sensors, and the power layer segments.

Starting at step 510, the control circuitry is operative to monitor the sensors while a user of the exosuit is performing an exercise movement to obtain exercise factors. The exercise factors can include any number of suitable data inputs that provide information regarding the movement and form of the user within the exosuit. For example, the movement can include data such as acceleration, velocity, position, and timing of the exosuit during the movement. The form can include position data of the exosuit at different times throughout the movement. The position data can be extrapolated to determine body positions such as back angle, shoulder position, arm position, knee position, thigh position, lumbar position, upper back position, hip angle, elbow position, and any other cues that are indicative of form.

The exercise factors may be associated with parameters to define an amount of leeway the movement or form can vary from an ideal movement or form. That is, a particular exercise movement may have an ideal biomechanical movement and form associated with it, and the user should endeavor to replicate that ideal biomechanical movement and form when performing the exercise. Since each person is different, the biomechanical movement for different body types will vary from one person to the next. The parameters may be adjusted to take these differences into account. For example, the parameters may be selected based on a user setup process in which the user may provide dimensions of his or her body parts.

At step 520, the control circuitry can analyze the exercise factors to determine whether the user is performing the exercise movement within parameters associated with the exercise movement. The control circuitry may collect the data from the sensors to obtain the exercise factors, including the movement and form. The control circuitry can compare the exercise factors to the parameters to determine whether the movement and/or form is within an acceptable deviation of the ideal biomechanical movement and form for the exercise.

At step 530, the control circuitry may communicate feedback that indicates whether the user is performing the exercise movement within the parameters associated with the movement. For example, if the user is performing the movement within the parameters, the control circuitry may cause the exosuit to provide positive feedback. In addition, the control circuitry can communicate with a user device, which can provide positive feedback via its touch screen or speaker based on the control circuitry's analysis of the sensor data. As another example, if the user is not performing the movement within the parameters, control circuitry may provide corrective feedback. For example, the control circuitry may selectively activate the appropriate power layer segments to reposition the user in the correct alignment. As another example, the control circuitry may cause the exosuit to provide corrective feedback by playing back a voice recording that targets the particular movement or form issues, or the exosuit may activate haptic feedback elements to indicate which regions are not in compliance with the exercise movement. In addition, the control circuitry can communicate with a user device, which can display an avatar of the user's position on a screen of a user device or a large screen such as a television.

It should be understood that the steps shown in FIG. 5 are illustrative and that additional steps may be added, and that the order of the steps may be rearranged.

Figure 6:
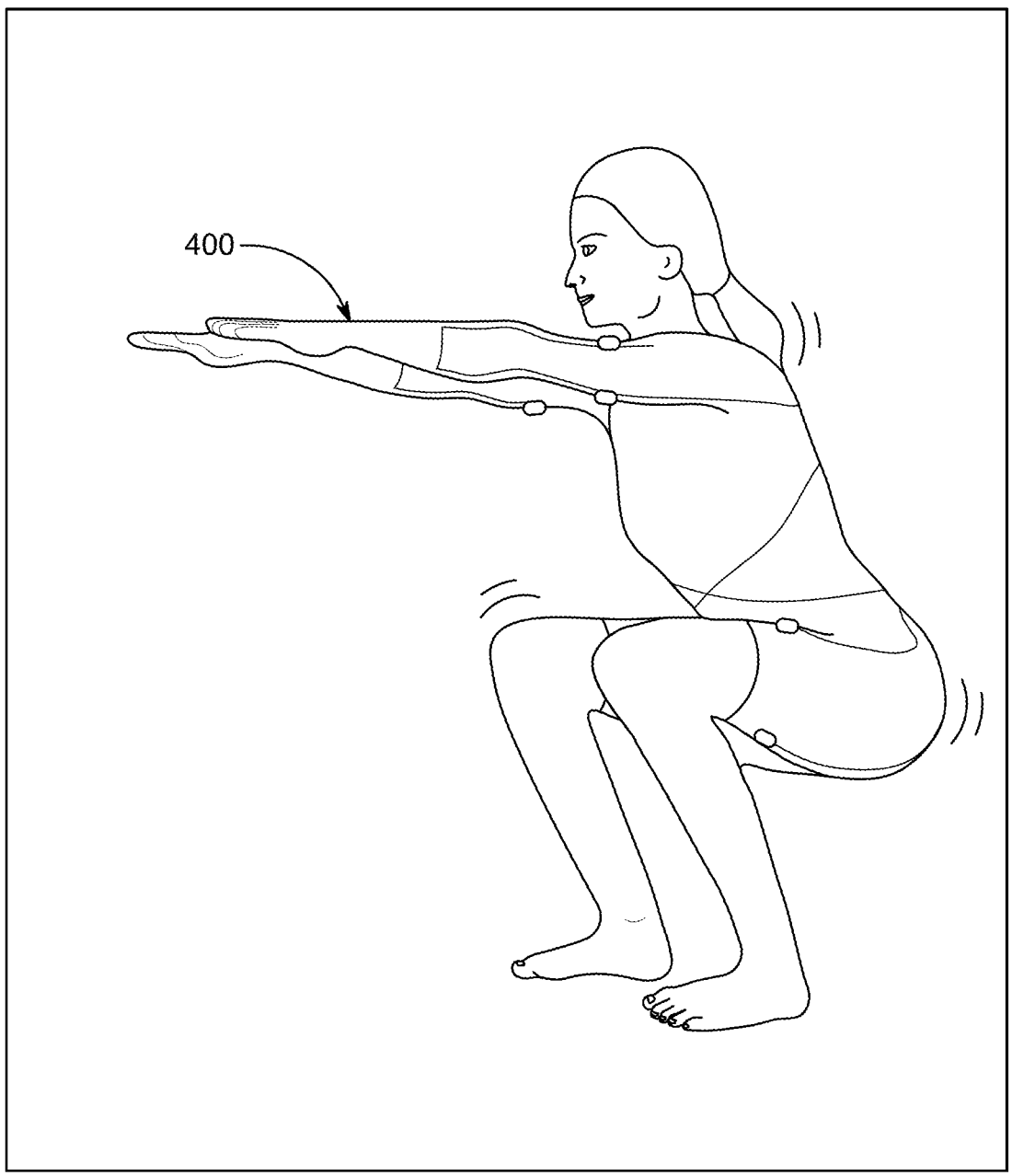
FIG. 6 shows an illustrative example in which an ARA exosuit provides resistance to the user while the user performs an exercise, according to an embodiment.

FIG. 6 shows an illustrative example in which ARA exosuit 400 provides resistance to the user while the user performs an exercise. Exosuit resistance may resist movement or actions being performed by the user of the exosuit to make the exercise more difficult for the user to perform, thus requiring the user to exert additional effort. The exosuit may provide resistance by activating power layer segments that oppose muscle groups that are needed to perform a particular exercise move. As the movement is performed, the control circuitry can dynamically control which power layer segments are activated to ensure that a minimal amount of resistance is provided by the exosuit.

As shown in FIG. 6, the user is performing an air squat. As the user performs the squat, the exosuit may provide resistance in the arms by attempting to pull the arms down as the user drops into the squat position. The user must resist this pull as she holds the arms up while she drops into the squat position. When the user rises up from the squat position, the exosuit may provide resistive forces that make it more difficult for the user to pull herself up out of the squat position.

Figure 7:
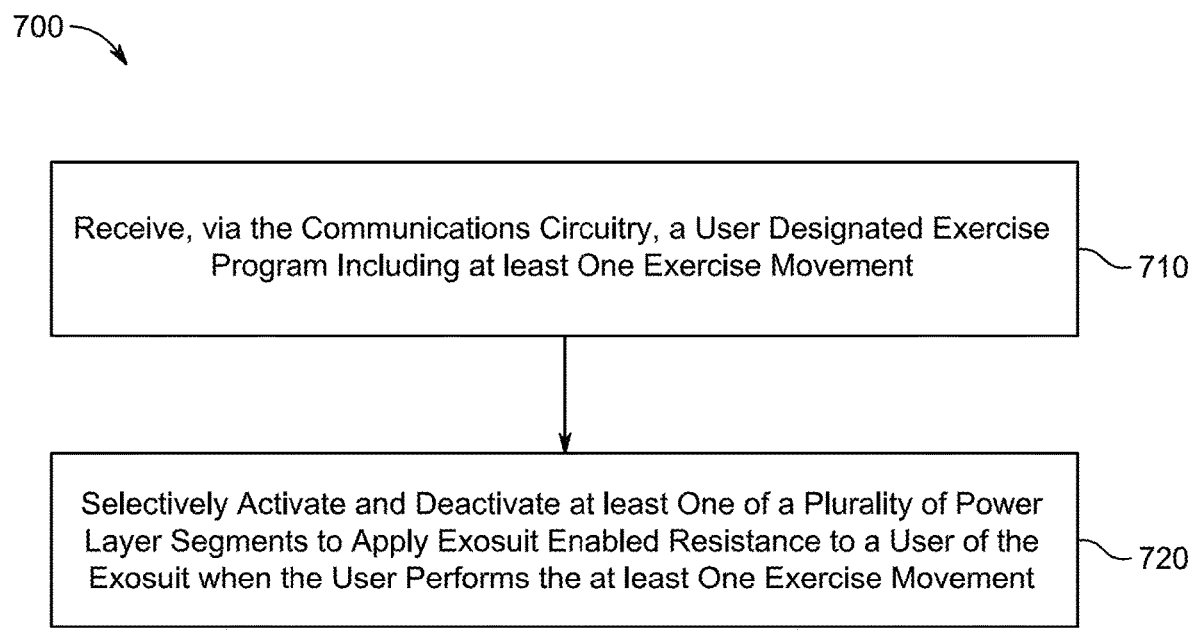
FIG. 7 shows an illustrative flowchart for providing alignment guidance using an exosuit according to an embodiment.

FIG. 7 shows an illustrative flowchart of process 700 for providing alignment guidance using an exosuit according to an embodiment. Process 700 may be implemented in an exosuit or in combination with an exosuit and a user device. The exosuit may embody the elements of exosuits discussed above such as in FIGS. 1A-1F and FIGS. 2A and 2B. The exosuit may include several sensors that are disposed throughout the suit and several power layer segments that mimic musculature anatomy movements of the human body. The exosuit may include communications circuitry and control circuitry coupled to the communications circuitry, the sensors, and the power layer segments.

Starting at step 710, a user designated exercise program including at least one exercise movement may be received via the communications circuitry. For example, the user may select an exercise program using a user device such as a smart phone. At step 720, the control circuitry can selectively activate and deactivate at least one of the plurality of power layer segments to apply exosuit enabled resistance to a user of the exosuit when the user performs the at least one exercise movement.

It should be understood that the steps shown in FIG. 7 are illustrative and that additional steps may be added, and that the order of the steps may be rearranged.

Figure 8A:
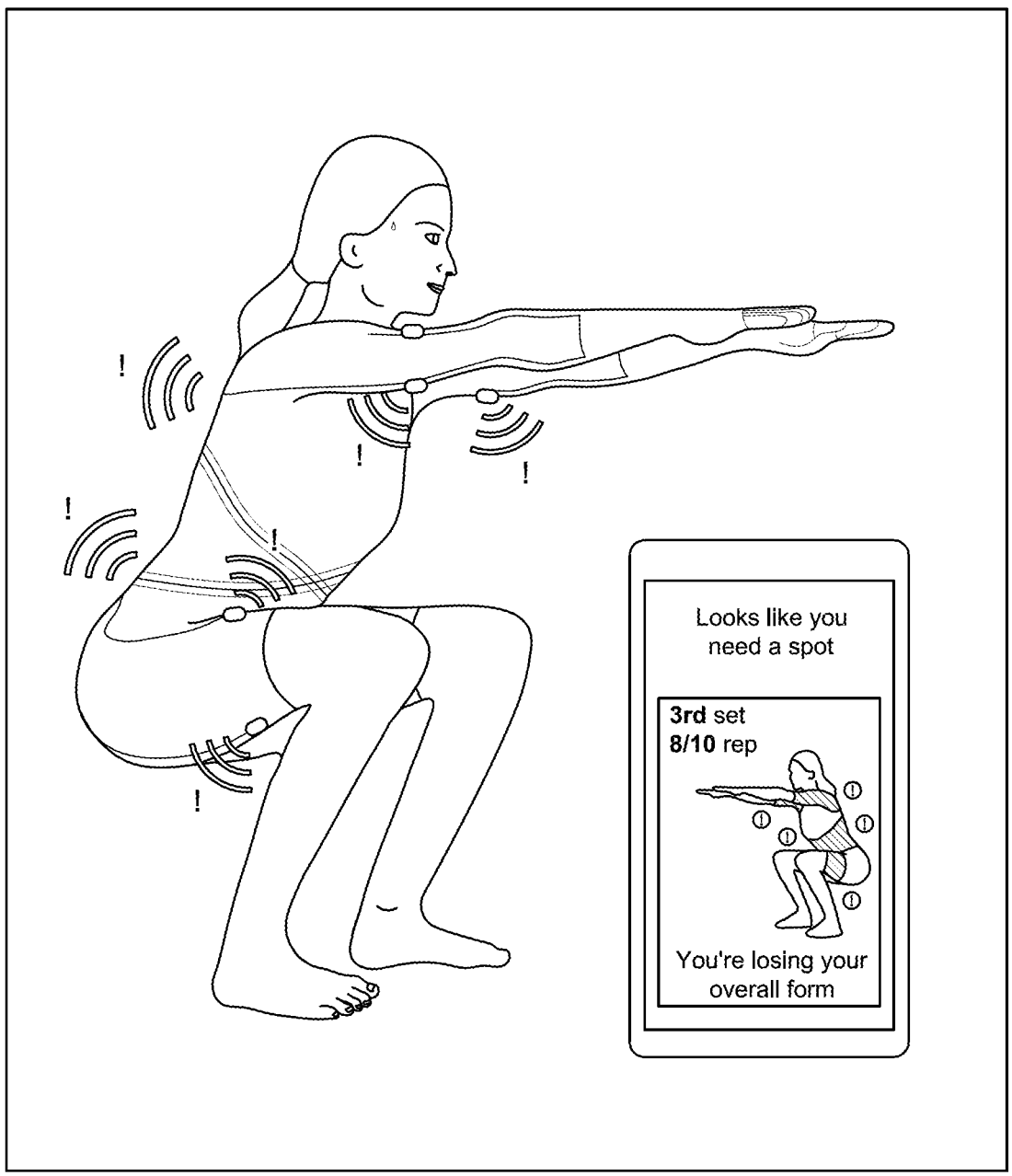
FIGS. 8A-8C show illustrative examples in which an ARA exosuit provides assistance to the user while the user performs an exercise, according to an embodiment.
Figure 8B:
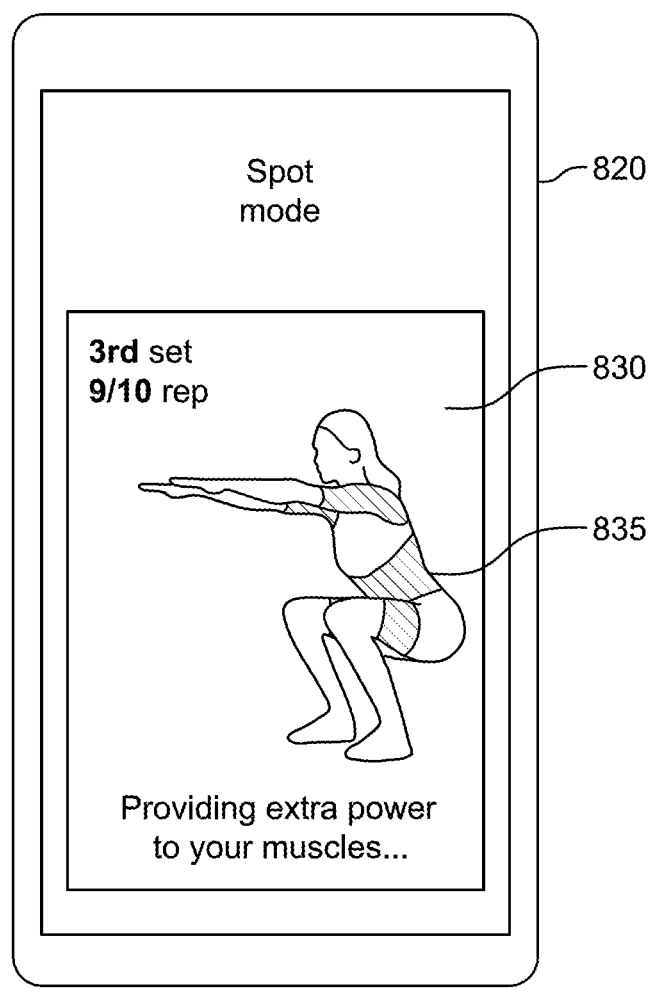
Figure 8C:
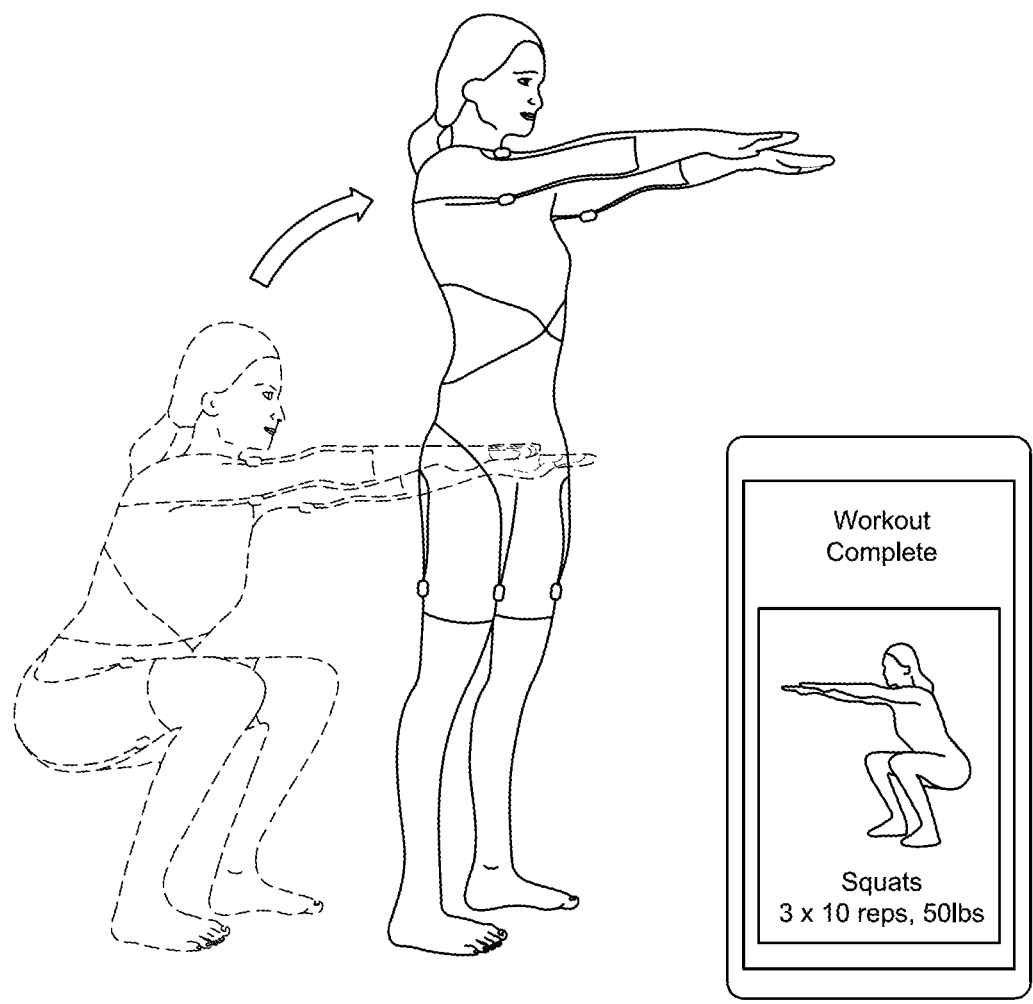

FIGS. 8A-8C show illustrative examples in which ARA exosuit 400 provides assistance to the user while the user performs an exercise. Exosuit assistance may supplement movement or actions being performed by the user of the exosuit to enable the user to complete the rep or set. Such assistance may be beneficial in enabling the user to obtain muscle gains that she may not otherwise be able to obtain without the help of a human spotter. The exosuit may serve the role of human spotter by providing assistance when and where it is needed.

Referring to FIG. 8A, the user is in a squat position, but the exosuit determines that the user is struggling to push up and out of the squat position. The exosuit may make such a determination by evaluating the sensor data. For example, the sensor data may indicate that the user has been in the squat position for over a period of time. As another example, when sensors may detect neuromuscular activity, but there is no movement, the control circuitry may determine that the user requires a spot. The exosuit may provide a notification that the user is struggling to maintain form or perform the movement. In addition, a user device 820 may also provide a notification that the user is struggling to maintain form or perform the movement.

FIG. 8B shows an illustrative screen 830 of user device 820. As shown, screen 830 indicates the exosuit has entered into "spot mode" and illustrates avatar 835. Avatar 835 may specify which power layer segments are being activated to spot the user. After spot mode is engaged, the user may be provided with muscle assistance to complete the rep or set.

Figure 9:
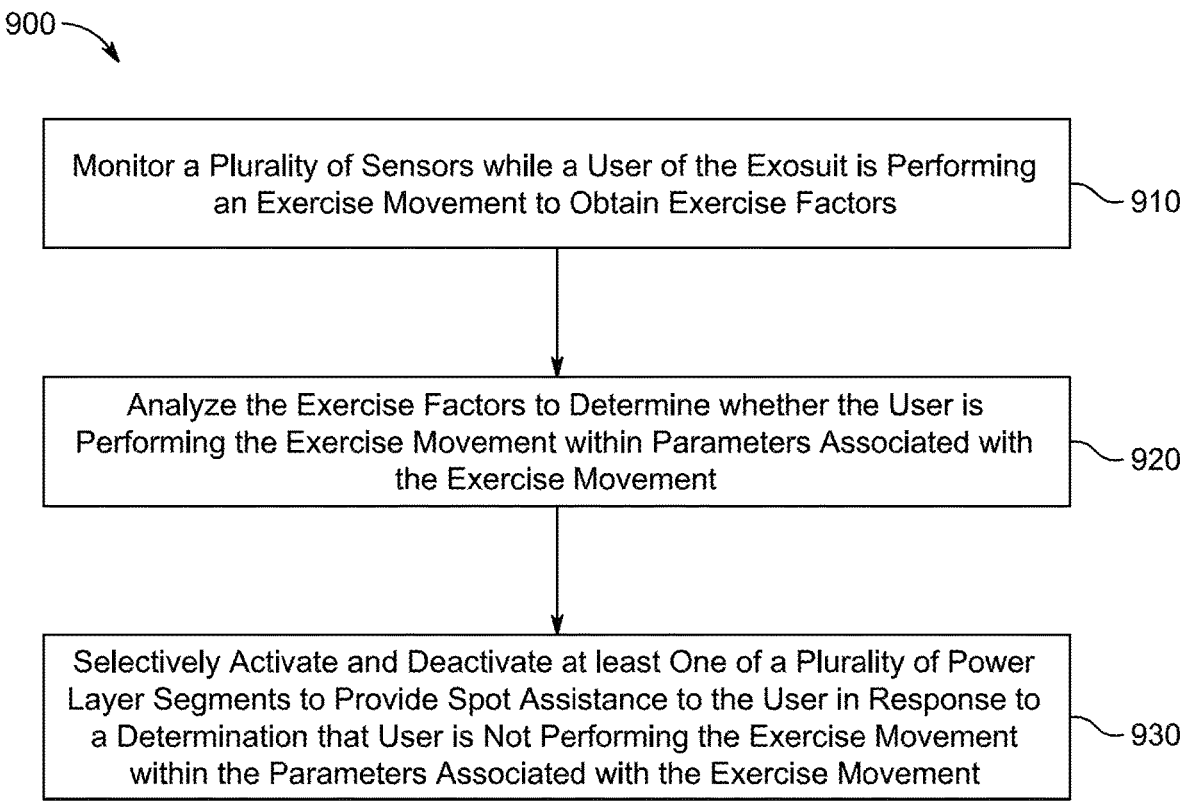
FIG. 9 shows an illustrative flowchart for providing alignment guidance using an exosuit according to an embodiment.

FIG. 9 shows an illustrative flowchart of process 900 for providing alignment guidance using an exosuit according to an embodiment. Process 900 may be implemented in an exosuit or in combination with an exosuit and a user device. The exosuit may embody the elements of exosuits discussed above such as in FIGS. 1A-1F and FIGS. 2A and 2B. The exosuit may include several sensors that are disposed throughout the suit and several power layer segments that mimic musculature anatomy movements of the human body. The exosuit may include communications circuitry and control circuitry coupled to the communications circuitry, the sensors, and the power layer segments.

Starting with step 910, the control circuitry can monitor the sensors while a user of the exosuit is performing an exercise movement to obtain exercise factors. At step 920, the control circuitry can analyze the exercise factors to determine whether the user is performing the exercise movement within parameters associated with the exercise movement. The same parameters discussed above in apply to the spot mode. At step 930, the control circuitry may selectively activate and deactivate at least one of the plurality of power layer segments to provide spot assistance to the user in response to a determination that the user is not performing the exercise movement within the parameters associated with the exercise movement.

It should be understood that the steps shown in FIG. 9 are illustrative and that additional steps may be added, and that the order of the steps may be rearranged.

Figure 10B:
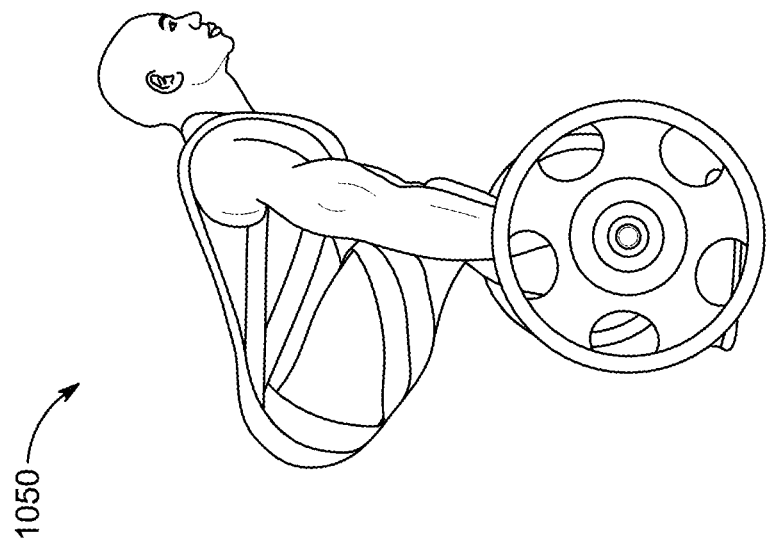
FIGS. 10A, 10B, 11A, 11B, 12A, 12B, 13A-13C show illustrative ARA exosuits according to various embodiments.
Figure 10A:
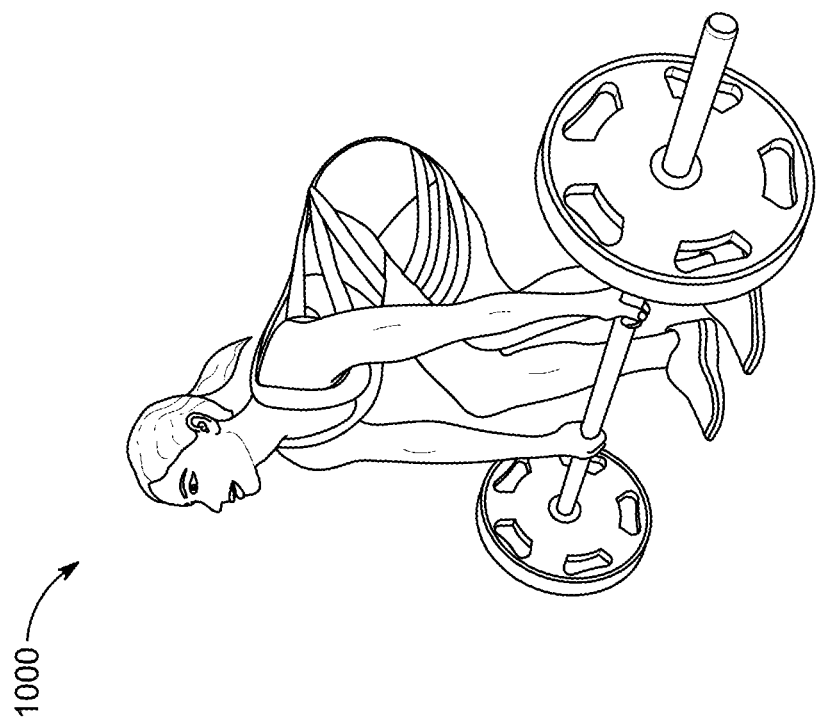

FIGS. 10A and 10B show illustrative ARA exosuits 1000 and 1050 according to various embodiments. Both exosuits 1000 and 1050 are worn by a user performing a deadlift exercise. The power layer segments, as shown by the lines spanning across the body, emphasize muscle assistance for abdominal muscles, back muscles, gluteal muscles, hip extensor muscles, and hip lateral support muscles.

Figure 11A:
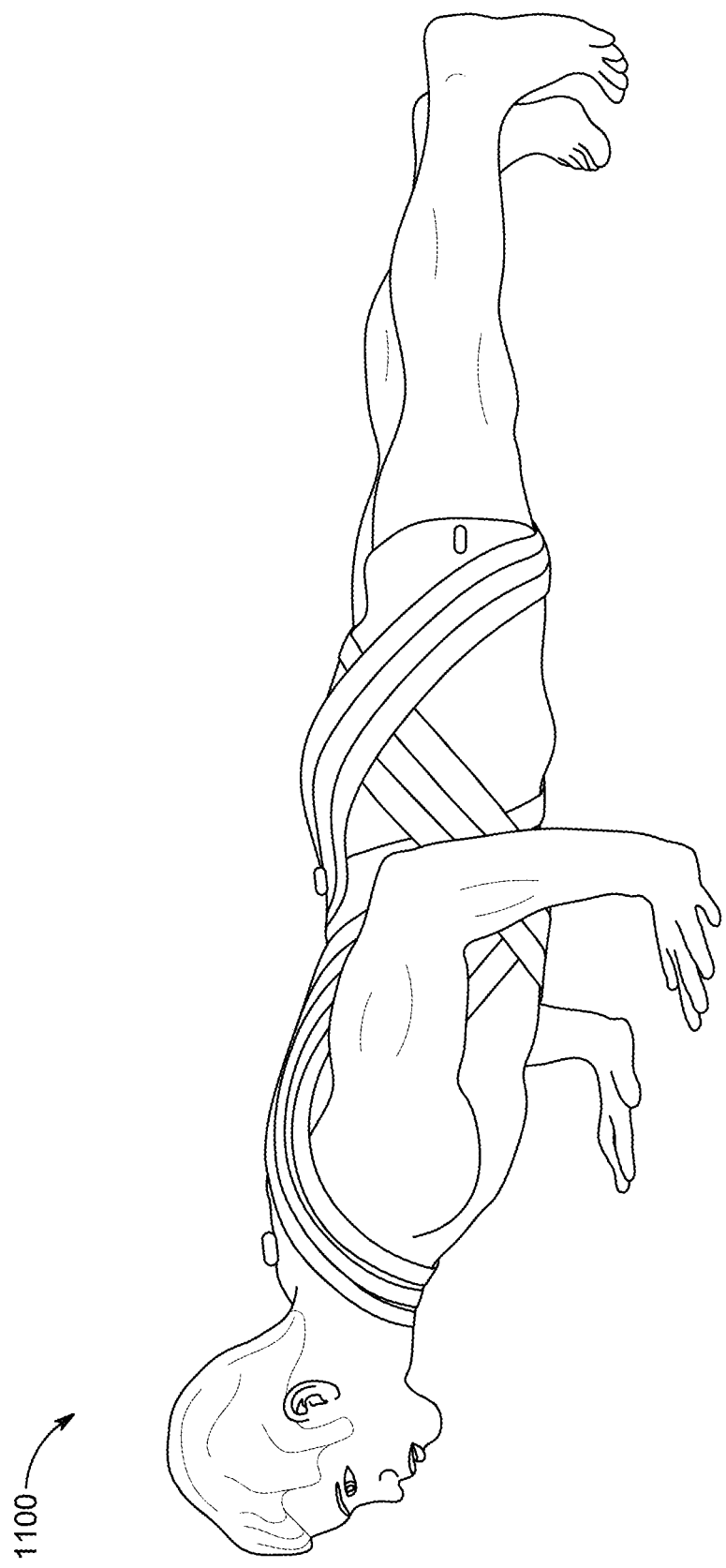
Figure 11B:
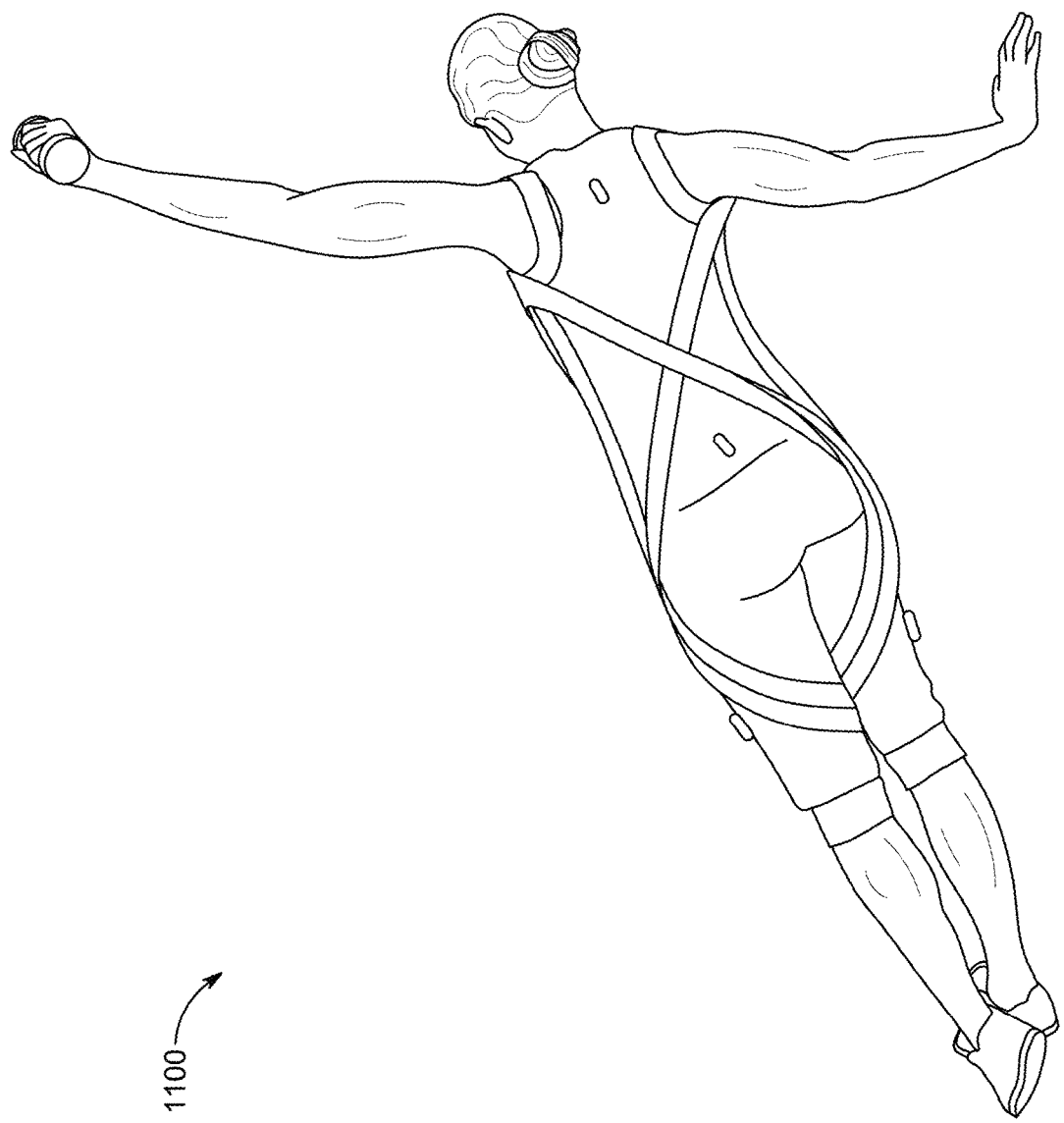

FIGS. 11A and 11B show an illustrative ARA exosuit 1100 having power layer segments that emphasize muscle assistance for upper back muscles, abdominal muscles, hip muscles, and hip support muscles.

Figure 12A:
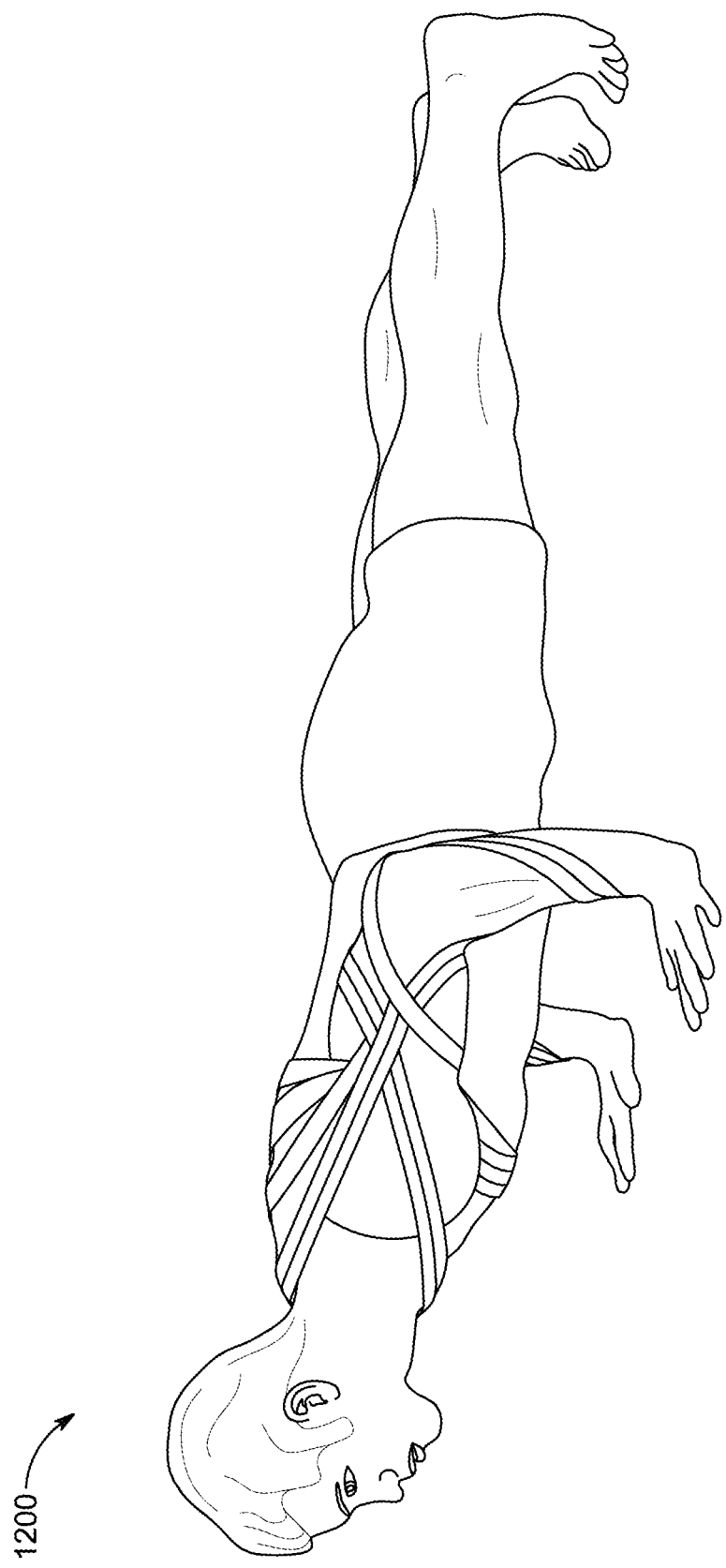
Figure 12B:

FIGS. 12A and 12B show an illustrative ARA exosuit 1200 having power layer segments that emphasize muscle assistance for shoulder muscles, anti muscles, and trapezii muscles.

Figure 13A:

FIG. 13A shows illustrative ARA exosuit 1300 having power layer segments that emphasize muscle assistance for shoulder, arms, and dorsal muscles.

Figure 13B:

FIG. 13B shows illustrative ARA exosuit 1330 having power layer segments that can provide a tunable resistance between two portions of the human body. As shown, the power layer segment may provide resistance to a user performing a squat move.

Figure 13C:
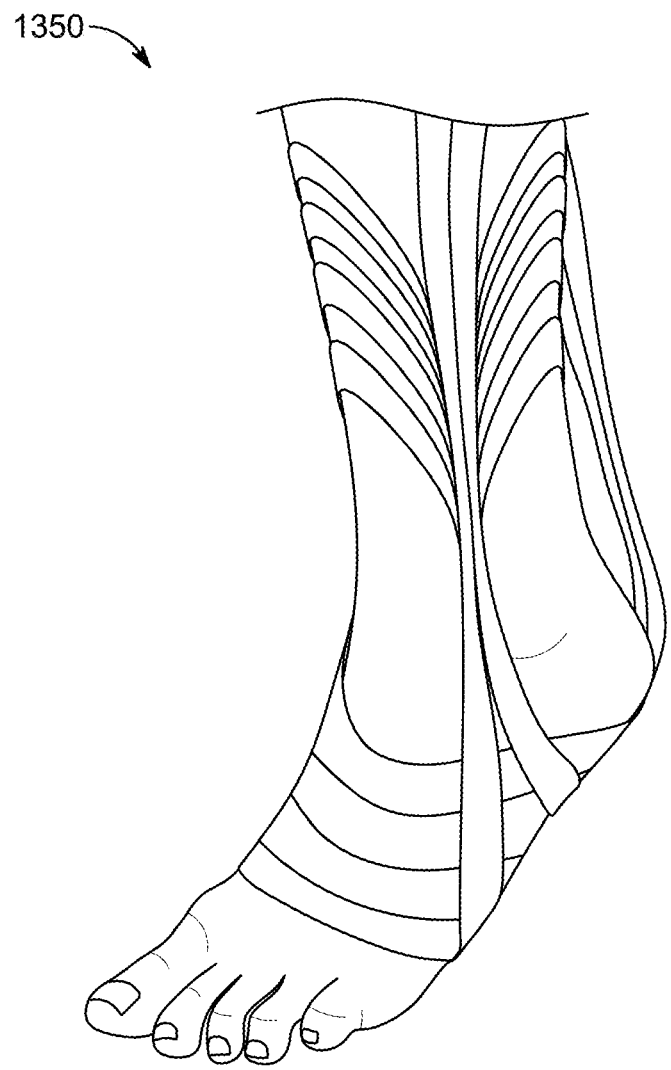

FIG. 13CB shows illustrative ARA exosuit 1350 power layer segments that emphasize muscle assistance for the ankle.

An exosuit can be operated by electronic controllers disposed on or within the exosuit or in wireless or wired communication with the exosuit. The electronic controllers can be configured in a variety of ways to operate the exosuit and to enable functions of the exosuit. The electronic controllers can access and execute computer-readable programs that are stored in elements of the exosuit or in other systems that are in direct or indirect communications with the exosuit. The computer-readable programs can describe methods for operating the exosuit or can describe other operations relating to a exosuit or to a wearer of a exosuit.

Figure 14:
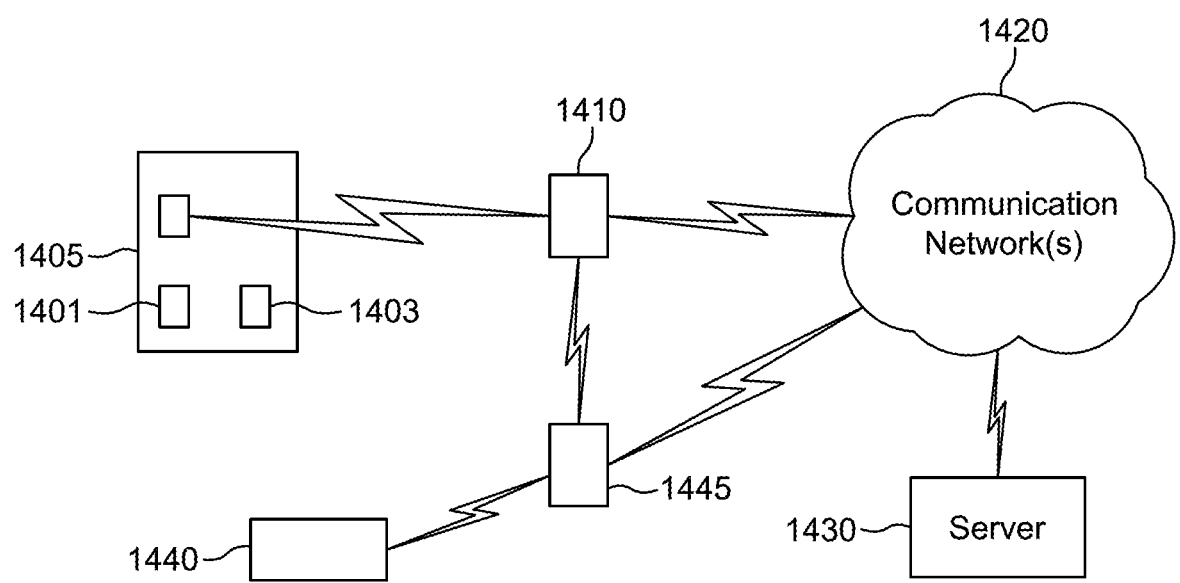
FIG. 14 illustrates a exosuit and system configured to communicate with the exosuit according to various embodiments.

FIG. 14 illustrates an example exosuit 1400 that includes actuators 1401, sensors 1403, and a controller configured to operate elements of exosuit 1400 (e.g., 1401, 1403) to enable functions of the exosuit 1400. The controller 1405 is configured to communicate wirelessly with a user interface

1410. The user interface 1410 is configured to present information to a user (e.g., a wearer of the exosuit 1400) and to the controller 1405 of the flexible exosuit or to other systems. The user interface 1410 can be involved in controlling and/or accessing information from elements of the exosuit 1400. For example, an application being executed by the user interface 1410 can access data from the sensors 1403, calculate an operation (e.g., to apply dorsiflexion stretch) of the actuators 1401, and transmit the calculated operation to the exosuit 1400. The user interface 1410 can additionally be configured to enable other functions; for example, the user interface 1410 can be configured to be used as a cellular telephone, a portable computer, an entertainment device, or to operate according to other applications.

The user interface 1410 can be configured to be removably mounted to the exosuit 1400 (e.g., by straps, magnets, Velcro, charging and/or data cables). Alternatively, the user interface 1410 can be configured as a part of the exosuit 1400 and not to be removed during normal operation. In some examples, a user interface can be incorporated as part of the exosuit 1400 (e.g., a touchscreen integrated into a sleeve of the exosuit 1400) and can be used to control and/or access information about the exosuit 1400 in addition to using the user interface 1810 to control and/or access information about the exosuit 1400. In some examples, the controller 1805 or other elements of the exosuit 1400 are configured to enable wireless or wired communication according to a standard protocol (e.g., Bluetooth, ZigBee, WiFi, LIE or other cellular standards, IRdA, Ethernet) such that a variety of systems and devices can be made to operate as the user interface 1410 when configured with complementary communications elements and computer-readable programs to enable such functionality.

The exosuit 1400 can be configured as described in example embodiments herein or in other ways according to an application. The exosuit 1400 can be operated to enable a variety of applications. The exosuit 1400 can be operated to enhance the strength of a wearer by detecting motions of the wearer (e.g., using sensors 1403) and responsively applying torques and/or forces to the body of the wearer (e.g., using actuators 1401) to increase the forces the wearer is able to apply to his/her body and/or environment. The exosuit 1400 can be operated to train a wearer to perform certain physical activities. For example, the exosuit 1400 can be operated to enable rehabilitative therapy of a wearer. The exosuit 1400 can operate to amplify motions and/or forces produced by a wearer undergoing therapy in order to enable the wearer to successfully complete a program of rehabilitative therapy. Additionally or alternatively, the exosuit 1400 can be operated to prohibit disordered movements of the wearer and/or to use the actuators 1801 and/or other elements (e.g., haptic feedback elements) to indicate to the wearer a motion or action to perform and/or motions or actions that should not be performed or that should be terminated. Similarly, other programs of physical training (e.g., dancing, skating, other athletic activities, vocational training) can be enabled by operation of the exosuit 1400 to detect motions, torques, or forces generated by a wearer and/or to apply forces, torques, or other haptic feedback to the wearer. Other applications of the exosuit 1400 and/or user interface 1410 are anticipated.

The user interface 1410 can additionally communicate with communications network(s) 1420. For example, the user interface 1410 can include a WiFi radio, an LTE transceiver or other cellular communications equipment, a wired modem, or some other elements to enable the user interface 1410 and exosuit 1400 to communicate with the Internet. The user interface 1410 can communicate through the communications network 1420 with a server 1430. Communication with the server 1430 can enable functions of the user interface 1410 and exosuit 1400. In some examples, the user interface 1410 can upload telemetry data (e.g., location, configuration of elements 1401, 1403 of the exosuit 1400, physiological data about a wearer of the exosuit 1400) to the server 1430.

In some examples, the server 1430 can be configured to control and/or access information from elements of the exosuit 1400 (e.g., 1401, 1403) to enable some application of the exosuit 1400. For example, the server 1430 can operate elements of the exosuit 1400 to move a wearer out of a dangerous situation if the wearer was injured, unconscious, or otherwise unable to move themselves and/or operate the exosuit 1400 and user interface 1410 to move themselves out of the dangerous situation. Other applications of a server in communications with a exosuit are anticipated.

The user interface 1410 can be configured to communicate with a second user interface 1445 in communication with and configured to operate a second flexible exosuit 1440. Such communication can be direct (e.g., using radio transceivers or other elements to transmit and receive information over a direct wireless or wired link between the user interface 1410 and the second user interface 1445). Additionally or alternatively, communication between the user interface 1410 and the second user interface 1445 can be facilitated by communications network(s) 1420 and/or a server 1430 configured to communicate with the user interface 1410 and the second user interface 1445 through the communications network(s) 1420.

Communication between the user interface 1410 and the second user interface 1445 can enable applications of the exosuit 1400 and second exosuit 1440. In some examples, actions of the exosuit 1400 and second flexible exosuit 1440 and/or of wearers of the exosuit 1400 and second exosuit 1440 can be coordinated. For example, the exosuit 1400 and second exosuit 1440 can be operated to coordinate the lifting of a heavy object by the wearers. The timing of the lift, and the degree of support provided by each of the wearers and/or the exosuit 1400 and second exosuit 1440 can be controlled to increase the stability with which the heavy object was carried, to reduce the risk of injury of the wearers, or according to some other consideration. Coordination of actions of the exosuit 1400 and second exosuit 1440 and/or of wearers thereof can include applying coordinated (in time, amplitude, or other properties) forces and/or torques to the wearers and/or elements of the environment of the wearers and/or applying haptic feedback (though actuators of the exosuits 1400, 1440, through dedicated haptic feedback elements, or through other methods) to the wearers to guide the wearers toward acting in a coordinated manner.

Coordinated operation of the exosuit 1400 and second exosuit 1440 can be implemented in a variety of ways. In some examples, one exosuit (and the wearer thereof) can act as a master, providing commands or other information to the other exosuit such that operations of the exosuit 1400, 1440 are coordinated. For example, the exosuit 1400, 1440 can be operated to enable the wearers to dance (or to engage in some other athletic activity) in a coordinated manner One of the exosuits can act as the 'lead', transmitting timing or other information about the actions performed by the 'lead' wearer to the other exosuit, enabling coordinated dancing motions to be executed by the other wearer. In some examples, a first wearer of a first exosuit can act as a trainer, modeling motions or other physical activities that a second wearer of a second exosuit can learn to perform. The first exosuit can detect motions, torques, forces, or other physical activities executed by the first wearer and can send information related to the detected activities to the second exosuit. The second exosuit can then apply forces, torques, haptic feedback, or other information to the body of the second wearer to enable the second wearer to learn the motions or other physical activities modeled by the first wearer. In some examples, the server 1430 can send commands or other information to the exosuits 1400, 1440 to enable coordinated operation of the exosuits 1400, 1440.

The exosuit 1400 can be operated to transmit and/or record information about the actions of a wearer, the environment of the wearer, or other information about a wearer of the exosuit 1400. In some examples, kinematics related to motions and actions of the wearer can be recorded and/or sent to the server 1430. These data can be collected for medical, scientific, entertainment, social media, or other applications. The data can be used to operate a system. For example, the exosuit 1400 can be configured to transmit motions, forces, and/or torques generated by a user to a robotic system (e.g., a robotic arm, leg, torso, humanoid body, or some other robotic system) and the robotic system can be configured to mimic the activity of the wearer and/or to map the activity of the wearer into motions, forces, or torques of elements of the robotic system. In another example, the data can be used to operate a virtual avatar of the wearer, such that the motions of the avatar mirrored or were somehow related to the motions of the wearer. The virtual avatar can be instantiated in a virtual environment, presented to an individual or system with which the wearer is communicating, or configured and operated according to some other application.

Conversely, the exosuit 1400 can be operated to present haptic or other data to the wearer. In some examples, the actuators 1401 (e.g., twisted string actuators, exotendons) and/or haptic feedback elements (e.g., EPAM haptic elements) can be operated to apply and/or modulate forces applied to the body of the wearer to indicate mechanical or other information to the wearer. For example, the activation in a certain pattern of a haptic element of the exosuit 1400 disposed in a certain location of the exosuit 1400 can indicate that the wearer had received a call, email, or other communications. In another example, a robotic system can be operated using motions, forces, and/or torques generated by the wearer and transmitted to the robotic system by the exosuit 1400. Forces, moments, and other aspects of the environment and operation of the robotic system can be transmitted to the exosuit 1400 and presented (using actuators 1401 or other haptic feedback elements) to the wearer to enable the wearer to experience force-feedback or other haptic sensations related to the wearer's operation of the robotic system. In another example, haptic data presented to a wearer can be generated by a virtual environment, e.g., an environment containing an avatar of the wearer that is being operated based on motions or other data related to the wearer that is being detected by the exosuit 1400.

Note that the exosuit 1400 illustrated in FIG. 14 is only one example of a exosuit that can be operated by control electronics, software, or algorithms described herein. Control electronics, software, or algorithms as described herein can be configured to control flexible exosuits or other mechatronic and/or robotic system having more, fewer, or different actuators, sensors or other elements. Further, control electronics, software, or algorithms as described herein can be configured to control exosuits configured similarly to or differently from the illustrated exosuit 1400. Further, control electronics, software, or algorithms as described herein can be configured to control flexible exosuits having reconfigurable hardware (i.e., exosuits that are able to have actuators, sensors, or other elements added or removed) and/or to detect a current hardware configuration of the flexible exosuits using a variety of methods.

A controller of a exosuit and/or computer-readable programs executed by the controller can be configured to provide encapsulation of functions and/or components of the flexible exosuit. That is, some elements of the controller (e.g., subroutines, drivers, services, daemons, functions) can be configured to operate specific elements of the exosuit (e.g., a twisted string actuator, a haptic feedback element) and to allow other elements of the controller (e.g., other programs) to operate the specific elements and/or to provide abstracted access to the specific elements (e.g., to translate a command to orient an actuator in a commanded direction into a set of commands sufficient to orient the actuator in the commanded direction). This encapsulation can allow a variety of services, drivers, daemons, or other computer-readable programs to be developed for a variety of applications of a flexible exosuits. Further, by providing encapsulation of functions of a flexible exosuit in a generic, accessible manner (e.g., by specifying and implementing an application programming interface (API) or other interface standard), computer-readable programs can be created to interface with the generic, encapsulated functions such that the computer-readable programs can enable operating modes or functions for a variety of differently-configured exosuit, rather than for a single type or model of flexible exosuit. For example, a virtual avatar communications program can access information about the posture of a wearer of a flexible exosuit by accessing a standard exosuit API. Differently-configured exosuits can include different sensors, actuators, and other elements, but can provide posture information in the same format according to the API. Other functions and features of a flexible exosuit, or other robotic, exoskeletal, assistive, haptic, or other mechatronic system, can be encapsulated by APIs or according to some other standardized computer access and control interface scheme.

Figure 15:
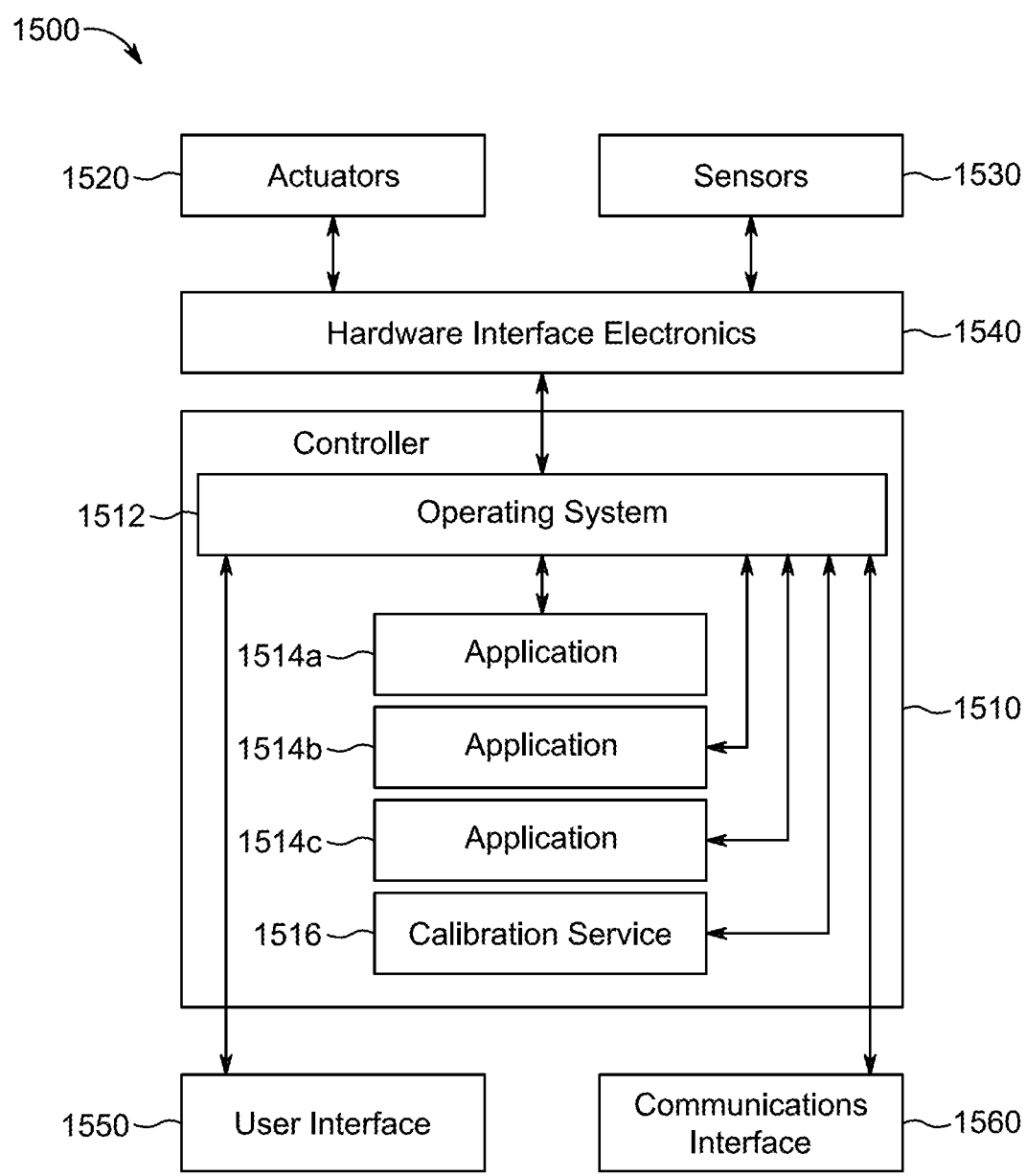
FIG. 15 illustrates a schematic of a control scheme for a exosuit according to various embodiments.

FIG. 15 is a schematic illustrating elements of an exosuit 1500 and a hierarchy of control or operating the exosuit 1500. The flexible exosuit includes actuators 1520 and sensors 1530 configured to apply forces and/or torques to and detect one or more properties of, respectively, the exosuit 1500, a wearer of the exosuit 1500, and/or the environment of the wearer. The exosuit 1500 additionally includes a controller 1510 configured to operate the actuators 1520 and sensors 1530 by using hardware interface electronics 1540. The hardware electronics interface 1540 includes electronics configured to interface signals from and to the controller 1510 with signals used to operate the actuators 1520 and sensors 1530. For example, the actuators 1520 can include exotendons, and the hardware interface electronics 1540 can include high-voltage generators, high-voltage switches, and high-voltage capacitance meters to clutch and un-clutch the exotendons and to report the length of the exotendons. The hardware interface electronics 1540 can include voltage regulators, high voltage generators, amplifiers, current detectors, encoders, magnetometers, switches, controlled-current sources, DACs, ADCs, feedback controllers, brushless motor controllers, or other electronic and mechatronic elements.

The controller 1510 additionally operates a user interface 1550 that is configured to present information to a user and/or wearer of the exosuit 1500 and a communications interface 1560 that is configured to facilitate the transfer of information between the controller 1510 and some other system (e.g., by transmitting a wireless signal). Additionally or alternatively, the user interface 1550 can be part of a separate system that is configured to transmit and receive user interface information to/from the controller 1510 using the communications interface 1560 (e.g., the user interface 1550 can be part of a cellphone).

The controller 1510 is configured to execute computer-readable programs describing functions of the flexible exosuit 1512. Among the computer-readable programs executed by the controller 1510 are an operating system 1512, applications 1514a, 1514b, 1514c, and a calibration service 1516. The operating system 1512 manages hardware resources of the controller 1510 (e.g., I/O ports, registers, timers, interrupts, peripherals, memory management units, serial and/or parallel communications units) and, by extension, manages the hardware resources of the exosuit 1500. The operating system 1512 is the only computer-readable program executed by the controller 1510 that has direct access to the hardware interface electronics 1540 and, by extension, the actuators 1520 and sensors 1530 of the exosuit 1500.

The applications 1514a, 1514b, 1514 are computer-readable programs that describe some function, functions, operating mode, or operating modes of the exosuit 1500. For example, application 1514 a can describe a process for transmitting information about the wearer's posture to update a virtual avatar of the wearer that includes accessing information on a wearer's posture from the operating system 1512, maintaining communications with a remote system using the communications interface 1560, formatting the posture information, and sending the posture information to the remote system. The calibration service 1516 is a computer-readable program describing processes to store parameters describing properties of wearers, actuators 1520, and/ or sensors 1530 of the exosuit 1500, to update those parameters based on operation of the actuators 1520, and/or sensors 1530 when a wearer is using the exosuit 1500, to make the parameters available to the operating system 1512 and/or applications 1514a, 1514b, 1514c, and other functions relating to the parameters. Note that applications 1514a, 1514b, 1514 and calibration service 1516 are intended as examples of computer-readable programs that can be run by the operating system 1512 of the controller 1510 to enable functions or operating modes of a exosuit 1500.

The operating system 1512 can provide for low-level control and maintenance of the hardware (e.g., 1520, 1530, 1540). In some examples, the operating system 1512 and/or hardware interface electronics 1540 can detect information about the exosuit 1500, the wearer, and/or the wearer's environment from one or more sensors 1530 at a constant specified rate. The operating system 1512 can generate an estimate of one or more states or properties of the exosuit 1500 or components thereof using the detected information. The operating system 1512 can update the generated estimate at the same rate as the constant specified rate or at a lower rate. The generated estimate can be generated from the detected information using a filter to remove noise, generate an estimate of an indirectly-detected property, or according to some other application. For example, the operating system 1512 can generate the estimate from the detected information using a Kalman filter to remove noise and to generate an estimate of a single directly or indirectly measured property of the exosuit 1500, the wearer, and/or the wearer's environment using more than one sensor. In some examples, the operating system can determine information about the wearer and/or exosuit 1500 based on detected information from multiple points in time. For example, the operating system 1500 can determine an eversion stretch and dorsiflexion stretch.

In some examples, the operating system 1512 and/or hardware interface electronics 1540 can operate and/or provide services related to operation of the actuators 1520. That is, in case where operation of the actuators 1520 requires the generation of control signals over a period of time, knowledge about a state or states of the actuators 1520, or other considerations, the operating system 1512 and/or hardware interface electronics 1540 can translate simple commands to operate the actuators 1520 (e.g., a command to generate a specified level of force using a twisted string actuator (TSA) of the actuators 1520) into the complex and/or state-based commands to the hardware interface electronics 1540 and/or actuators 1520 necessary to effect the simple command (e.g., a sequence of currents applied to windings of a motor of a TSA, based on a starting position of a rotor determined and stored by the operating system 1510, a relative position of the motor detected using an encoder, and a force generated by the TSA detected using a load cell).

In some examples, the operating system 1512 can further encapsulate the operation of the exosuit 1500 by translating a system-level simple command (e.g., a commanded level of force tension applied to the footplate) into commands for multiple actuators, according to the configuration of the exosuit 1500. This encapsulation can enable the creation of general-purpose applications that can effect a function of an exosuit (e.g., allowing a wearer of the exosuit to stretch his foot) without being configured to operate a specific model or type of exosuit (e.g., by being configured to generate a simple force production profile that the operating system 1512 and hardware interface electronics 1540 can translate into actuator commands sufficient to cause the actuators 1520 to apply the commanded force production profile to the footplate).

The operating system 1512 can act as a standard, multi-purpose platform to enable the use of a variety of exosuits having a variety of different hardware configurations to enable a variety of mechatronic, biomedical, human interface, training, rehabilitative, communications, and other applications. The operating system 1512 can make sensors 1530, actuators 1520, or other elements or functions of the exosuit 1500 available to remote systems in communication with the exosuit 1500 (e.g., using the communications interface 1560) and/or a variety of applications, daemons, services, or other computer-readable programs being executed by operating system 1512. The operating system 1512 can make the actuators, sensors, or other elements or functions available in a standard way (e.g., through an API, communications protocol, or other programmatic interface) such that applications, daemons, services, or other computer-readable programs can be created to be installed on, executed by, and operated to enable functions or operating modes of a variety of flexible exosuits having a variety of different configurations. The API, communications protocol, or other programmatic interface made available by the operating system 1512 can encapsulate, translate, or otherwise abstract the operation of the exosuit 1500 to enable the creation of such computer-readable programs that are able to operate to enable functions of a wide variety of differently-configured flexible exosuits.

Additionally or alternatively, the operating system 1512 can be configured to operate a modular flexible exosuit system (i.e., a flexible exosuit system wherein actuators, sensors, or other elements can be added or subtracted from a flexible exosuit to enable operating modes or functions of the flexible exosuit). In some examples, the operating system 1512 can determine the hardware configuration of the exosuit 1500 dynamically and can adjust the operation of the exosuit 1500 relative to the determined current hardware configuration of the exosuit 1500. This operation can be performed in a way that was 'invisible' to computer-readable programs (e.g., 1514a, 1514b, 1514c) accessing the functionality of the exosuit 1500 through a standardized programmatic interface presented by the operating system 1512. For example, the computer-readable program can indicate to the operating system 1512, through the standardized programmatic interface, that a specified level of torque was to be applied to an ankle of a wearer of the exosuit 1500. The operating system 1512 can responsively determine a pattern of operation of the actuators 1520, based on the determined hardware configuration of the exosuit 1500, sufficient to apply the specified level of torque to the ankle of the wearer.

In some examples, the operating system 1512 and/or hardware interface electronics 1540 can operate the actuators 1520 to ensure that the exosuit 1500 does not operate to directly cause the wearer to be injured and/or elements of the exosuit 1500 to be damaged. In some examples, this can include not operating the actuators 1520 to apply forces and/or torques to the body of the wearer that exceeded some maximum threshold. This can be implemented as a watchdog process or some other computer-readable program that can be configured (when executed by the controller 1510) to monitor the forces being applied by the actuators 1520 (e.g., by monitoring commands sent to the actuators 1520 and/or monitoring measurements of forces or other properties detected using the sensors 1530) and to disable and/or change the operation of the actuators 1520 to prevent injury of the wearer. Additionally or alternatively, the hardware interface electronics 1540 can be configured to include circuitry to prevent excessive forces and/or torques from being applied to the wearer (e.g., by channeling to a comparator the output of a load cell that is configured to measure the force generated by a TSA, and configuring the comparator to cut the power to the motor of the ISA when the force exceeded a specified level).

In some examples, operating the actuators 1520 to ensure that the exosuit 1500 does not damage itself can include a watchdog process or circuitry configured to prevent over-current, over-load, over-rotation, or other conditions from occurring that can result in damage to elements of the exosuit 1500. For example, the hardware interface electronics 1540 can include a metal oxide varistor, breaker, shunt diode, or other element configured to limit the voltage and/or current applied to a winding of a motor.

Note that the above functions described as being enabled by the operating system 1512 can additionally or alternatively be implemented by applications 1514a, 1514b, 1514c, services, drivers, daemons, or other computer-readable programs executed by the controller 1500. The applications, drivers, services, daemons, or other computer-readable programs can have special security privileges or other properties to facilitate their use to enable the above functions.

The operating system 1512 can encapsulate the functions of the hardware interface electronics 1540, actuators 1520, and sensors 1530 for use by other computer-readable programs (e.g., applications 1514a, 1514b, 1514c, calibration service 1516, by the user (through the user interface 1550), and/or by some other system (i.e., a system configured to communicate with the controller 1510 through the communications interface 1560). The encapsulation of functions of the exosuit 1500 can take the form of application programming interfaces (APIs), i.e., sets of function calls and procedures that an application running on the controller 1510 can use to access the functionality of elements of the exosuit 1500. In some examples, the operating system 1512 can make available a standard 'exosuit API' to applications being executed by the controller 1510. The 'exosuit API' can enable applications 1514a, 1514b, 1514c to access functions of the exosuit 1500 without requiring those applications 1514a, 1514b, 1514c to be configured to generate whatever complex, time-dependent signals are necessary to operate elements of the exosuit 1500 (e.g., actuators 1520, sensors 1530).

The 'exosuit API' can allow applications 1514a, 1514b, 1514c to send simple commands to the operating system 1512 (e.g., 'begin storing mechanical energy from the ankle of the wearer when the foot of the wearer contacts the ground') in such that the operating system 1512 can interpret those commands and generate the command signals to the hardware interface electronics 1540 or other elements of the exosuit 1500 that are sufficient to effect the simple commands generated by the applications 1514a, 1514b, 1514c (e.g., determining whether the foot of the wearer has contacted the ground based on information detected by the sensors 1530, responsively applying high voltage to an exotendon that crosses the user's ankle).

The 'exosuit API' can be an industry standard (e.g., an ISO standard), a proprietary standard, an open-source standard, or otherwise made available to individuals that can then produce applications for exosuits. The 'exosuit API' can allow applications, drivers, services, daemons, or other computer-readable programs to be created that are able to operate a variety of different types and configurations of exosuits by being configured to interface with the standard 'exosuit API' that is implemented by the variety of different types and configurations of exosuits. Additionally or alternatively, the 'exosuit API' can provide a standard encapsulation of individual exosuit-specific actuators (i.e., actuators that apply forces to specific body segments, where differently-configured exosuits may not include an actuator that applies forces to the same specific body segments) and can provide a standard interface for accessing information on the configuration of whatever exosuit is providing the 'exosuit API'. An application or other program that accesses the 'exosuit API' can access data about the configuration of the exosuit (e.g., locations and forces between body segments generated by actuators, specifications of actuators, locations and specifications of sensors) and can generate simple commands for individual actuators (e.g., generate a force of 30 newtons for 50 milliseconds) based on a model of the exosuit generated by the application and based on the information on the accessed data about the configuration of the exosuit. Additional or alternate functionality can be encapsulated by an 'exosuit API' according to an application.

Applications 1514a, 1514b, 1514c can individually enable all or parts of the functions and operating modes of a flexible exosuit described herein. For example, an application can enable haptic control of a robotic system by transmitting postures, forces, torques, and other information about the activity of a wearer of the exosuit 1500 and by translating received forces and torques from the robotic system into haptic feedback applied to the wearer (i.e., forces and torques applied to the body of the wearer by actuators 1520 and/or haptic feedback elements). In another example, an application can enable a wearer to locomote more efficiently by submitting commands to and receiving data from the operating system 1512 (e.g., through an API) such that actuators 1520 of the exosuit 1500 assist the movement of the user, extract negative work from phases of the wearer's locomotion and inject the stored work to other phases of the wearer's locomotion, or other methods of operating the exosuit 1500. Applications can be installed on the controller 1510 and/or on a computer-readable storage medium included in the exosuit 1500 by a variety of methods. Applications can be installed from a removable computer-readable storage medium or from a system in communication with the controller 1510 through the communications interface 1560. In some examples, the applications can be installed from a web site, a repository of compiled or un-compiled programs on the Internet, an online store (e.g., Google Play, Mines App Store), or some other source. Further, functions of the applications can be contingent upon the controller 1510 being in continuous or periodic communication with a remote system (e.g., to receive updates, authenticate the application, to provide information about current environmental conditions).

The exosuit 1500 illustrated in FIG. 15 is intended as an illustrative example. Other configurations of flexible exosuits and of operating systems, kernels, applications, drivers, services, daemons, or other computer-readable programs are anticipated. For example, an operating system configured to operate a exosuit can include a real-time operating system component configured to generate low-level commands to operate elements of the exosuit and a non-real-time component to enable less time-sensitive functions, like a clock on a user interface, updating computer-readable programs stored in the exosuit, or other functions. A exosuit can include more than one controller; further, some of those controllers can be configured to execute real-time applications, operating systems, drivers, or other computer-readable programs (e.g., those controllers were configured to have very short interrupt servicing routines, very fast thread switching, or other properties and functions relating to latency-sensitive computations) while other controllers are configured to enable less time-sensitive functions of a flexible exosuit. Additional configurations and operating modes of a exosuit are anticipated. Further, control systems configured as described herein can additionally or alternatively be configured to enable the operation of devices and systems other than exosuit; for example, control systems as described herein can be configured to operate robots, rigid exosuits or exoskeletons, assistive devices, prosthetics, or other mechatronic devices.

Control of actuators of an exosuit can be implemented in a variety of ways according to a variety of control schemes. Generally, one or more hardware and/or software controllers can receive information about the state of the flexible exosuit, a wearer of the exosuit, and/or the environment of the exosuit from sensors disposed on or within the exosuit and/or a remote system in communication with the exosuit. The one or more hardware and/or software controllers can then generate a control output that can be executed by actuators of the exosuit to effect a commanded state of the exosuit and/or to enable some other application. One or more software controllers can be implemented as part of an operating system, kernel, driver, application, service, daemon, or other computer-readable program executed by a processor included in the exosuit.

In some embodiments, a powered assistive exosuit intended primarily for assistive functions can also be adapted to perform exosuit functions. Embodiments of such an assistive exosuit typically include FLAs approximating muscle groups such as hip flexors, gluteal/hip extensors, spinal extensors, or abdominal muscles. In the assistive modes of these exosuits, these FLAs provide assistance for activities such as moving between standing and seated positions, walking, and postural stability. Actuation of specific FLAs within such an exosuit system may also provide stretching assistance. Typically, activation of one or more FLAs approximating a muscle group can stretch the antagonist muscles. For example, activation of one or more FLAs approximating the abdominal muscles might stretch the spinal extensors, or activation of one or more FLAs approximating gluteal/hip extensor muscles can stretch the hip flexors. The exosuit may be adapted to detect when the wearer is ready to initiate a stretch and perform an automated stretching regimen; or the wearer may indicate to the suit to initiate a stretching regimen.

It can be appreciated that assistive exosuits may have multiple applications. Assistive exosuits may be prescribed for medical applications. These may include therapeutic applications, such as assistance with exercise or stretching regimens for rehabilitation, disease mitigation or other therapeutic purposes. Mobility-assistance devices such as wheelchairs, walkers, crutches and scooters are often prescribed for individuals with mobility impairments. Likewise, an assistive exosuit may be prescribed for mobility assistance for patients with mobility impairments. Compared with mobility assistance devices such as wheelchairs, walkers, crutches and scooters, an assistive exosuit may be less bulky, more visually appealing, and conform with activities of daily living such as riding in vehicles, attending community or social functions, using the toilet, and common household activities.

An assistive exosuit may additionally function as primary apparel, fashion items or accessories. The exosuit may be stylized for desired visual appearance. The stylized design may reinforce visual perception of the assistance that the exosuit is intended to provide. For example, an assistive exosuit intended to assist with torso and upper body activities may present a visual appearance of a muscular torso and upper body. Alternatively, the stylized design may be intended to mask or camouflage the functionality of the assistive exosuit through design of the base layer, electro/mechanical integration or other design factors.

Similarly to assistive exosuits intended for medically prescribed mobility assistance, assistive exosuits may be developed and utilized for non-medical mobility assistance, performance enhancement and support. For many, independent aging is associated with greater quality of life, however activities may become more limited with time due to normal aging processes. An assistive exosuit may enable aging individuals living independently to electively enhance their abilities and activities. For example, gait or walking assistance could enable individuals to maintain routines such as social walking or golf. Postural assistance may render social situations more comfortable, with less fatigue. Assistance with transitioning between seated and standing positions may reduce fatigue, increase confidence, and reduce the risk of falls. These types of assistance, while not explicitly medical in nature, may enable more fulfilling, independent living during aging processes.

Athletic applications for an assistive exosuit are also envisioned. In one example, an exosuit may be optimized to assist with a particular activity, such as cycling. In the cycling example, FLAs approximating gluteal or hip extensor muscles may be integrated into bicycle clothing, providing assistance with pedaling. The assistance could be varied based on terrain, fatigue level or strength of the wearer, or other factors. The assistance provided may enable increased performance, injury avoidance, or maintenance of performance in the case of injury or aging. It can be appreciated that assistive exosuits could be optimized to assist with the demands of other sports such as running, jumping, swimming, skiing, or other activities. An athletic assistive exosuit may also be optimized for training in a particular sport or activity. Assistive exosuits may guide the wearer in proper form or technique, such as a golf swing, running stride, skiing form, swimming stroke, or other components of sports or activities. Assistive exosuits may also provide resistance for strength or endurance training. The provided resistance may be according to a regimen, such as high intensity intervals.

Assistive exosuit systems as described above may also be used in gaming applications. Motions of the wearer, detected by the suit, may be incorporated as a game controller system. For example, the suit may sense wearer's motions that simulate running, jumping, throwing, dancing, fighting, or other motions appropriate to a particular game. The suit may provide haptic feedback to the wearer, including resistance or assistance with the motions performed or other haptic feedback to the wearer.

Assistive exosuits as described above may be used for military or first responder applications. Military and first responder personnel are often to be required to perform arduous work where safety or even life may be at stake. An assistive exosuit may provide additional strength or endurance as required for these occupations. An assistive exosuit may connect to one or more communication networks to provide communication services for the wearer, as well as remote monitoring of the suit or wearer.

Assistive exosuits as described above may be used for industrial or occupational safety applications. Exosuits may provide more strength or endurance for specific physical tasks such as lifting or carrying or repetitive tasks such as assembly line work. By providing physical assistance, assistive exosuits may also help avoid or prevent occupational injury due overexertion or repetitive stress.

Assistive exosuits as described above may also be configured as home accessories. Home accessory assistive exosuits may assist with household tasks such as cleaning or yard work, or may be used for recreational or exercise purposes. The communication capabilities of an assistive exosuit may connect to a home network for communication, entertainment or safety monitoring purposes.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art can appreciate that the conception, upon which this disclosure is based, may readily be utilized as a basis for the designing of other structures, systems, methods and media for carrying out the several purposes of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

What is claimed is:

1. An exercise assistance system for use on a human body, the system comprising:
    an exosuit configured to be worn on the human body as a garment, the exosuit comprising:
        a plurality of sensors;
        a plurality of power layer segments that mimic musculature anatomy and movements of the human body;
        communications circuitry; and
        control circuitry coupled to the communications circuitry, the plurality of sensors, and the power layer segments, wherein the control circuitry is operative to:
            receive, via the communications circuitry, a user designated exercise program including at least one exercise movement; and
            selectively activate and deactivate at least one of the plurality of power layer segments to apply exosuit enabled resistance to a user of the exosuit when the user performs the at least one exercise movement, wherein the applied exosuit enabled resistance is applied such that a perceived level of increased effort required of the user is nearly imperceptible, yet is sufficient in magnitude to result in an improvement of a fitness level of the user over time.

2. The system of claim 1, wherein the plurality of power layer segments are operative to apply varying levels of resistance to the user.

3. The system of claim 1, wherein the at least one exercise movement requires activation of protagonist muscles, and wherein a subset of the power layer segments emulate activation of antagonist muscles associated with the at least one exercise movement to provide the resistance.

4. The system of claim 1, wherein each of the plurality of power layer segments comprises an array of flexible linear actuators that are secured to load distribution members.

5. The system of claim 1, wherein each of the plurality of power layer segments comprises a flexible linear actuator that is secured to load distribution members.

6. The system of claim 1, wherein each of the plurality of power layer segments comprises:
    a flexdrive subsystem that is secured to a first load distribution member;
    a twisted string coupled to the flexdrive subsystem and secured to a second load distribution member; and
    power/communication lines coupled to the flexdrive subsystem.

7. The system of claim 6, wherein the twisted string is aligned in conjunction with a muscle of the user.

8. An exercise assistance system for use on a human body, the system comprising:
    an exosuit configured to be worn on the human body as a next-to-skin garment, the exosuit comprising:
        a plurality of sensors;
        a plurality of power layer segments that mimic musculature anatomy and movements of the human body;
        communications circuitry; and
        control circuitry coupled to the communications circuitry, the plurality of sensors, and the power layer segments, wherein the control circuitry is operative to:
            receive body type parameters during a user setup process in which a user provides dimensions of his or her body;

monitor the plurality of sensors while the user of the exosuit is performing an exercise movement to obtain exercise factors;

adjusting the exercise factors based on the body type parameters;

analyze the adjusted exercise factors to determine whether the user is performing the exercise movement within parameters associated with the exercise movement;

communicate feedback that indicates whether the user is performing the exercise movement factors within the parameters; and selectively activate a subset of the plurality of power layer segments to reposition the user to a correct alignment in response to a determination that the exercise factors are not within the parameters, wherein the correct alignment enhances proprioceptive feedback for the user.

9. The system of claim 8, wherein the communicated feedback comprises audio feedback, visual feedback, or haptic feedback.

10. The system of claim 8, wherein the exercise factors comprise movement factors and form factors.

11. The system of claim 8, wherein the exercise factors are adjusted to compensate for dimensions of the user of the exosuit.

12. The system of claim 8, wherein each of the plurality of power layer segments comprises:
 a flexdrive subsystem that is secured to a first load distribution member;
 a twisted string coupled to the flexdrive subsystem and secured to a second load distribution member; and
 power/communication lines coupled to the flexdrive subsystem.

13. An exercise assistance system for use on a human body, the system comprising:
 an exosuit configured to be worn on the human body, the exosuit comprising:
  a plurality of sensors including a neuromuscular sensor operative to detect neuromuscular activity;
  a plurality of power layer segments that mimic musculature anatomy and movements of the human body;
  communications circuitry; and
  control circuitry coupled to the communications circuitry, the plurality of sensors, and the power layer segments, wherein the control circuitry is operative to:
   monitor the plurality of sensors, including the neuromuscular sensor, while a user of the exosuit is performing an exercise movement to obtain movement factors and neuromuscular activity;
   analyze the movement factors to determine whether the user is performing the exercise movement within parameters associated with the exercise movement; and
   selectively activate and deactivate at least one of the plurality of actuators to provide spot assistance to the user in response to a determination that that user is not performing the exercise movement within the parameters associated with the exercise movement and that neuromuscular activity associated with the exercise movement is monitored.

14. The system of claim 13, wherein the spot assistance enable the user to complete the exercise movement.

15. The system of claim 13, wherein each of the plurality of power layer segments comprises:
 a flexdrive subsystem that is secured to a first load distribution member;
 a twisted string coupled to the flexdrive subsystem and secured to a second load distribution member; and
 power/communication lines coupled to the flexdrive subsystem.

* * * * *